(12) United States Patent
Call et al.

(10) Patent No.: US 6,951,147 B2
(45) Date of Patent: Oct. 4, 2005

(54) OPTIMIZING ROTARY IMPACT COLLECTORS

(75) Inventors: Patrick T. Call, West Richland, WA (US); Vanessa M. Kenning, Kennewick, WA (US); Charles J. Call, Albuquerque, NM (US)

(73) Assignee: Mesosystems Technology, Inc., Albuquerque, NM (US)

( * ) Notice: Subject to any disclaimer, the term of this patent is extended or adjusted under 35 U.S.C. 154(b) by 0 days.

(21) Appl. No.: 10/601,315

(22) Filed: Jun. 20, 2003

(65) Prior Publication Data

US 2004/0025604 A1 Feb. 12, 2004

Related U.S. Application Data

(63) Continuation-in-part of application No. 09/775,872, filed on Feb. 1, 2001, now Pat. No. 6,729,196, which is a continuation-in-part of application No. 09/265,619, filed on Mar. 10, 1999, now Pat. No. 6,267,016.

(51) Int. Cl.[7] .................................................. G01N 1/00
(52) U.S. Cl. .................................................. 73/863.22
(58) Field of Search ........................ 73/863.22, 863.23, 73/863.24, 863.25, 28.04–28.06; 416/223 R, 234, 244 R, 246, 131, 179, 182–187, 197 R, 197 A, 197 B, 197 C, 202; 96/413, 265, 282; 417/423.1, 424.1, 424.2

(56) References Cited

U.S. PATENT DOCUMENTS

| 3,633,405 | A |   | 1/1972 | Noll ............................. 73/28 |
| 5,144,175 | A | * | 9/1992 | Craggs ....................... 310/63 |
| 5,669,811 | A | * | 9/1997 | Zaniewski .................. 454/16 |
| 5,925,960 | A | * | 7/1999 | Hayes ........................ 310/211 |
| 5,949,001 | A |   | 9/1999 | Willeke ..................... 73/865.5 |
| 6,267,016 | B1 |  | 7/2001 | Call et al. ................ 73/863.22 |
| 6,392,313 | B1 | * | 5/2002 | Epstein et al. .............. 290/52 |

* cited by examiner

Primary Examiner—Robert Raevis
(74) Attorney, Agent, or Firm—Ronald M. Anderson

(57) ABSTRACT

The present invention relates to optimizing the configuration of rotary impact collectors and devices in which such rotary impact collectors are employed. Rotary impact collectors are formed out of base plate upon which a plurality of vanes are mounted. One aspect of the present invention is a combined impact collector and fan in which the ratio of vane height to impeller diameter is in the range of about 0.01 to about 0.2. Preferably, the vanes are evenly spaced around the impeller so as to present a balanced load to the motor. Other performance enhancing elements include the use of truncated vanes, configurations optimized for injection molding fabrication, controlling the orientation of the vanes to reduce the formation of vortex forces, and enhancements configured to increase the ability to collected particles rinsed off such impellers.

30 Claims, 14 Drawing Sheets

OPTIMIZING ROTARY IMPACT COLLECTORS

RELATED APPLICATIONS

This application is a continuation-in-part of a patent application Ser. No. 09/775,872, filed on Feb. 1, 2001, now U.S. Pat. No. 6,729,196, which is itself a continuation-in-part of U.S. patent application Ser. No. 09/265,619 filed Mar. 10, 1999, now U.S. Pat. No. 6,267,016, the benefits of the filing dates of which are hereby claimed under 35 U.S.C. § 120.

GOVERNMENT RIGHTS

This invention was made under contract with the United States Department of Defense, under Contract Nos. DAAM01-97-C-0036 and M67854-00-C-3023, and the United States government may have certain rights in the invention.

FIELD OF THE INVENTION

This invention generally relates to chemical sampling using a combination impact collector and fan, and more specifically, to optimizing the performance of such rotary impact collectors.

BACKGROUND OF THE INVENTION

Sample acquisition and sample analysis are frequently performed as two disparate processes, since in situations that are not time critical, it is generally acceptable to take one or more samples, and to transport those samples to an analytical laboratory for analysis. Environmental air quality and water quality samples are often handled in such a fashion. However, there are many situations in which the ability to take an environmental air sample, and to analyze that sample immediately, are critical to health and safety. Measuring the air quality in poorly ventilated spaces such as mines, determining the presence of chemical and/or biological agents on the battlefield, or after an actual or suspected terrorist attack, are examples of situations in which sampling and analysis should be performed as quickly as possible, preferably by employing an integrated sampling and sensing apparatus that can provide and immediate indication of a life threatening substance in the environment.

There are many examples in the art of integrated sampling and detection apparatus. Dräger-Tubes, which are manufactured by Drägerwerk AG, Lübeck), are one well-known example of an integrated sampling and detection system. These devices are used to measure the concentration of specific gases and vapors in real time. Over 200 different Dräger tubes are available for measuring more than 500 different contaminants. The design and principle of operation of each Dräger-Tubes is the same in every case. A chemical reagent system is housed in an enclosed clear glass tube; and the reagent system reacts by changing color when exposed to a specific gas or vapor. The concentration of the substance is characterized by the length of discoloration within the tube and can be read off directly from a scale printed on the glass tube. Different amounts of air must be drawn through the tube, depending on the type and sensitivity of the reagent systems used. The volume of ambient air that must be drawn through the tube by a Dräger pump is stated on each tube. This prior art chemical sampling and detection system thus consists of a Dräger-Tube and a corresponding Dräger pump.

Other integrated air sampling and detection systems specifically designed to detect trace gases in air include electrochemical sensors for the measurement of gases such as CO, $H_2S$, $O_2$, $Cl_2$, $SO_2$, $NO_2$ etc, infrared sensors for the measurement of $CO_2$, $CH_4$ or alkanes, and catalytic (pellistor) gas sensors for measuring flammable gases.

One drawback of the prior art integrated sampling and detection devices is that the target of interest is often present in the sampled environment in extremely small amounts. Acquiring a good sample of a reagent at low concentrations is problematic. Even if the sensor is capable of detecting minute levels of an agent of interest, without a high quality and readily obtainable representative sample, the capabilities of the sensing system are inefficiently utilized. Even worse, an inadequate sample of a hazardous material can cause a detection device to falsely indicate the absence of that material.

The difficulty in obtaining a good quality sample is particularly evident with respect to sampling for airborne particulates or aerosols. For example, aerosols comprising small droplets of liquid dispersed into air are not easily analyzed unless the aerosol materials are separated from the air and concentrated in a sample that can then be accurately analyzed. As used herein, the term "particulates" (and its singular form "particulate") will be understood to include aerosols, liquids, solids, or semi-solids that are sufficiently small to be dispersed within and carried about in air or other gases and may include inorganic or organic chemicals, or living materials, e.g., bacterial cells or spores. Also, the term particulates refers to solids or semi-solids introduced into a liquid that is then dispersed within air as an aerosol mist so that the solids are carried within the liquid droplets comprising the aerosol mist.

Generally, it is difficult to identify materials comprising particulates entrained in a gaseous fluid unless the particulates can be collected and concentrated in a specimen suitable for analysis by separating them from the air or other gaseous fluid. One significant application in which extremely low levels of particulates need to be sampled and analyzed quickly is to provide combat troops with individual sampling units, that either include their own sensor, or which can be read in the field under combat conditions.

Particle impact devices are commonly used for collecting particulates from gaseous streams in which they are dispersed. These collectors "sweep" a large volume of air, and concentrate any particulates collected to provide a high quality representative sample. Several different types of particle impact collectors are available. Functionally, these particle impact collectors generally employ circuitous paths with many abrupt changes of direction along the passages through which a particulate-laden fluid flows. The particulates, being substantially more massive than the molecules of the fluid in which they are entrained, fail to negotiate the abrupt turns in these passages and are thus separated from the moving fluid stream, collecting on the surfaces that they impact. In the presently available types of particle impact collectors, there is generally a trade off between simplicity and efficiency.

Stationary impact collectors that employ a fan to force air against the impact surface are relatively simple, but are somewhat less efficient than would be desired. Rotating arm collectors are more efficient, yet are also more complex, in that they require both the rotating impact collector and a fan to be independently driven.

It would therefore be desirable to provide a simple and efficient particle impact collector that is capable of yielding a high quality representative sample of particulates or aerosols. Such a device is described in commonly assigned, co-pending U.S. patent application Ser. No. 09/265,619, entitled "Impact Particulate Collector Using A Rotary Impeller For Collecting Particulates And Moving A Fluid," which was filed Mar. 10, 1999, the specification and drawings of which are hereby specifically incorporated herein by reference. It would further be desirable to integrate such a sampling device with a sensor to provide a portable system capable of rapidly detecting the presence of an agent of interest, so that the sample that is collected does not need to be sent to a laboratory facility for analysis. The prior art does not teach or suggest a portable integrated sampler and sensor unit that employs a rotary impeller used to both collect particulates and move a fluid through the unit.

Furthermore, it would desirable to optimize the design of such a rotary impact collector to enhance its performance. The prior art does not teach or suggest how such optimization can be achieved.

SUMMARY OF THE INVENTION

The present invention relates to optimizing the configuration of rotary impact collectors and devices in which such rotary impact collectors are employed. Rotary impact collectors are formed out of base plate upon which a plurality of vanes are mounted. The combined particle impact collector and fan is readily fabricated by machining or injection molding, among other techniques.

Rotary impact collectors can be beneficially employed as a combined particle impact collector and fan to both drive a gaseous fluid into a collection unit and to collect particulates. The rotary impact collector is mounted into a housing defining a fluid passage for conveying a gaseous fluid, and is drivingly coupled to a prime mover, such as an electric motor. When the motor is energized, a particulate laden fluid is drawn into the fluid passage, and particles are removed from the fluid by impaction with the vanes. A primary application of these collector devices is in monitoring ambient air to detect trace particulates and aerosols. Samples of particulates that are thus collected can be taken to offsite laboratories for analysis, or detection units can be integrated into the collection units for detecting specific substances in real time. Larger rotary impact collectors can be placed into units for sampling rooms, while smaller rotary impact collectors can be used to provide a personal unit sufficiently small to be readily carried about by one person.

One aspect of the present invention is a combined impact collector and fan in which the ratio of vane height to impeller diameter is in the range of about 0.01 to about 0.2. Preferably, the vanes are evenly spaced around the impeller so as to present a balanced load to the motor.

Generally the combined impact collector and fan (i.e., the impeller) is disposed within a housing such that an opening in the housing will be disposed above a center of the impellers base plate. Another aspect of the present invention is an impeller configured to reduce the formation of a vortex in the fluid drawn into the housing. Such a vortex would undesirably impart angular velocity to the entrained particulates, changing the momentum of the particulates, and reducing the likelihood that such particulates will impact the impeller vanes as desired. One embodiment of an impeller for reducing the formation of such a vortex controls the location of the impeller vanes relative to the opening, such that no portion of the impeller vanes overlaps with the openings. Such openings are generally disposed over the center of the impeller base plate. For impellers to be utilized in such housings, preferably the impeller vanes formed on the impeller base plate do not extend inward beyond the circumference of an opening disposed above the center of the impeller base plate. Most preferably, no portion of the impeller vanes are disposed on the center portion of the impeller-based plate corresponding to the circumference of such an opening disposed above the center of the impeller base plate.

Another impeller configuration that will reduce the undesirable formation of a vortex is impellers that contain a plurality of truncated impeller vanes. Truncated impeller vanes are smaller in length than other impeller vanes. Such truncated impeller vanes can range in length from about 10% to about 90% of the length of a "normal" impeller vane. Any ratio of truncated impeller vanes can be used in proportion to the number of impeller vanes employed.

The basic configuration of an impeller is a base plate and a plurality of vanes. Some embodiments can include a top plate, which increases impaction efficiency of the impeller by eliminating the tendency of particles to travel over the top of the impeller vanes (thus avoiding impaction). However, the mass of such a top plate can undesirably increase the mass of the impeller, and the load upon the prime mover. Therefore, unless it is acceptable to use a larger motor (which can accommodate a larger load), it is preferable to not employ such a top plate. When a larger motor or a slower rotational rate is acceptable, then it is preferable to utilize such a top plate, to increase impaction efficiency.

When the impeller is disposed within a housing, a gap exists between the an upper plane of the impeller (either the tops of the vanes or the top surface of the top plate, if a top plate is employed) and an upper inner surface of the housing. If such a gap does not exist, frictional forces between the opposed surfaces will impair performance and operation of the device. A similar gap must exist between the lower face of the impeller and lower inner surface of the housing. If the impeller is fabricated using machining, then tolerances can be readily be controlled such that a very small gap is designed, and machining the impeller within the defined tolerances to ensure a gap is always present is not difficult. However, if the impeller is formed using a process that cannot be controlled as tightly (such as injection molding), it is possible for the impeller produced to vary so much from the specified design so that the impeller intrudes into the required gap. Thus, the tolerance for gap must be less than the expected variation in manufacturing of the parts (the housing and the impeller). Preferably, the design height of the gap is at least about 2 mm, and more preferably at least about 2.2 mm.

Particularly when impellers are to be produced using injection molding, the impeller vane should be designed with "draft", which is laterally extending material at the base of each feature to accommodate removal from the injection mold. In addition, it is preferable if the impeller vanes do not extend all the way to the outer edge of the impeller base plate, but rather stop at least about 1 mm before the outer edge.

In some collection devices in which an impeller can be beneficially employed, a wash liquid will be introduced into the housing, to rinse collected particles of the vanes of the impeller. When such a rinse liquid is introduced into the housing to rinse the surfaces of the impeller, the recovery efficiency is adversely affected if any liquid remains in the housing. Even if particles are successfully recovered from rinsed surfaces and entrained into the liquid, these particles are regarded as having never been collected since if a portion of the liquid is inaccessible. Preferably, the housing in which the impeller is disposed includes a slope in a bottom surface, such that fluid preferentially drains by force of gravity out of the housing. A common location where portions of such a rinse liquid can be trapped is in the annular region located at the intersection of the upper surface and side surfaces of the housing. In this region, air velocity is slow and liquid that enters this region tends to adhere to the walls and cease motion. This problem can be minimized by providing inwardly curving or inwardly angled inner surfaces of the housing at this location. Similarly, other regions inside the cavity that would benefit from providing an inwardly curving or inwardly angled surface occur at the bottom of the housing.

To utilize such a rinse liquid, a nozzle needs to be disposed adjacent to the impeller. In practice, it is preferable to locate such a nozzle proximate the inside edge of the impeller vanes, rather than to locate the nozzle proximate the opening in the housing, or proximate a center of the impeller plate.

In collection device embodiments that are configured to include a volume of rinse fluid, it is desirable to add a sensor to monitor the level of rinse liquid in a rinse reservoir. During the rinsing process, rinse liquid can evaporate due to friction and heat inside the housing. Consequently, the total amount of rinse liquid present in the apparatus decreases over time, which can adversely affect recovery efficiency. In such cases, it is beneficial to also include a make-up reservoir storing additional rinse liquid. In some embodiments, the sensor can be coupled to a microcontroller that determines the requisite action of associated pumps and valves necessary to achieve the desired operation. The microcontroller can further be coupled to a motor to increase or decrease the rotational speed of the impeller, or to halt the motion of the impeller in the event that the liquid level has fallen below the predetermined level and cannot be increased.

Yet another aspect of the present invention includes a filter in air sampling devise including an impeller. Such a filter will be disposed to so that all incoming air passes through the filter before reaching the impeller. In one embodiment the filter is a size-exclusion membrane, which contains pores of a certain size such that particles larger than the pores cannot pass through the membrane. Another example of a filter is a magnetic membrane with very large pores. In this case, the membrane blocks very few particles based on size-exclusion, but removes all or nearly all magnetic particles, such as iron filings. Note that iron filings can significantly increase the load on the motor, as iron is very dense. Another example of a beneficial filter is an affinity-based membrane. Such a membrane would also have very large pores, excluding few particles based on size. However, the membrane would include a chemical coating, such as an antibody, that would selectively remove certain target particles from the air based on molecular binding. Still another example of a filter is a membrane containing a chemical adsorbent, to selectively adsorb chemical vapors from the incoming air. Preferably the filter is removable for replacement, cleaning, or recovery of the collected material.

Yet another aspect of the invention enhances the flow of gaseous fluid within a collection device including an impeller. Sloped surfaces are employed in the housing and the impeller. The upper portion of the housing at the opening can be sloped, such that the slope begins at the periphery of the opening and extends radially outward. The inner surface of the housing, proximate the opening, is preferably a convex cone, with the highest part of the cone at the bottom peripheral edge of the opening, and the lowest part of the cone at the intersection of the upper surface of the housing and the side surfaces of the housing. If the impeller includes a top plate, the top plate preferably is replaced with a cone of the same pitch as the inner surface of the housing. The impeller vanes preferably adopt the same pitch, becoming taller toward the center of the impeller base plate, and shorter at the outer edge of the base plate. The advantage of this slope is the acceleration of the air that occurs as it moves from the center of the base plate to the outer edge of base plate. In the un-sloped configuration, the cross-sectional area of the airflow increases in this direction, meaning that airflow would normally decelerate. By adding the slope, however, the cross sectional area can be made to increase less, stay constant, or even decrease, meaning that the air velocity can be made less decelerating, constant, or accelerating.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

The foregoing aspects and many of the attendant advantages of this invention will become more readily appreciated as the same becomes better understood by reference to the following detailed description, when taken in conjunction with the accompanying drawings, wherein.

Figure 13:
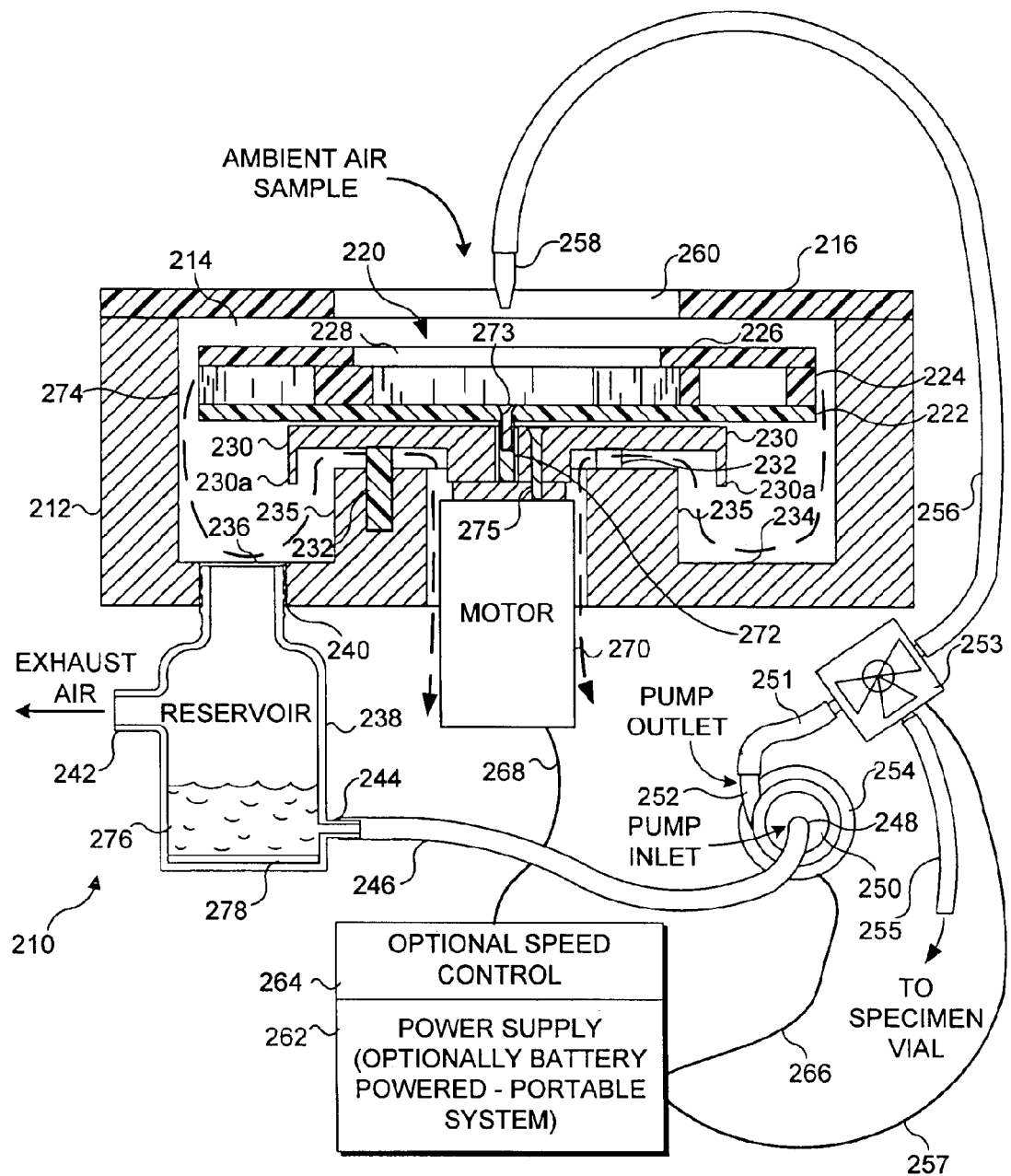
FIG. 13 is a cross-sectional elevational view of the embodiment shown in FIG. 12.
Figure 15:
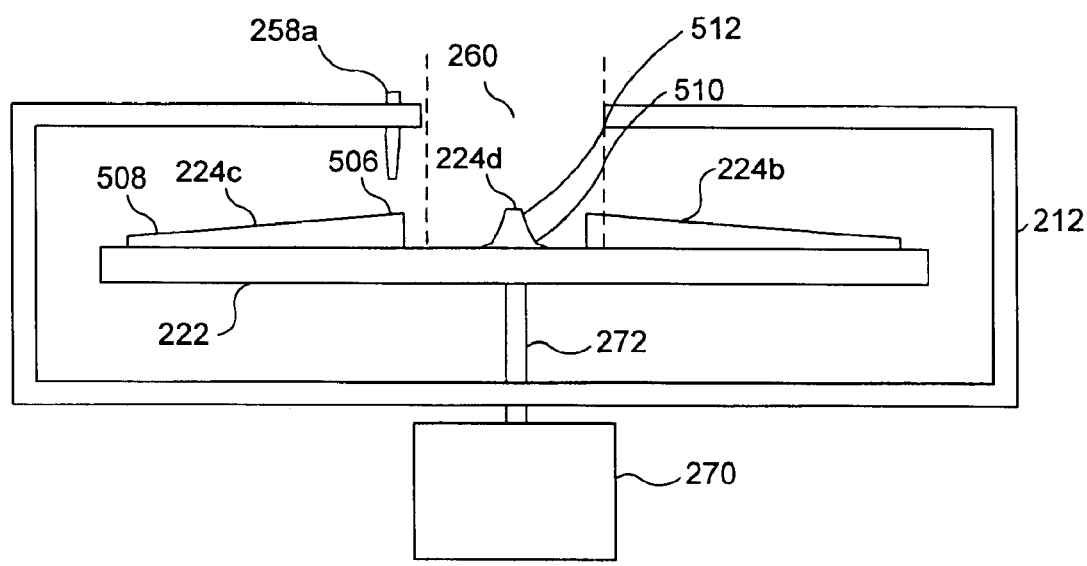
Figure 16:
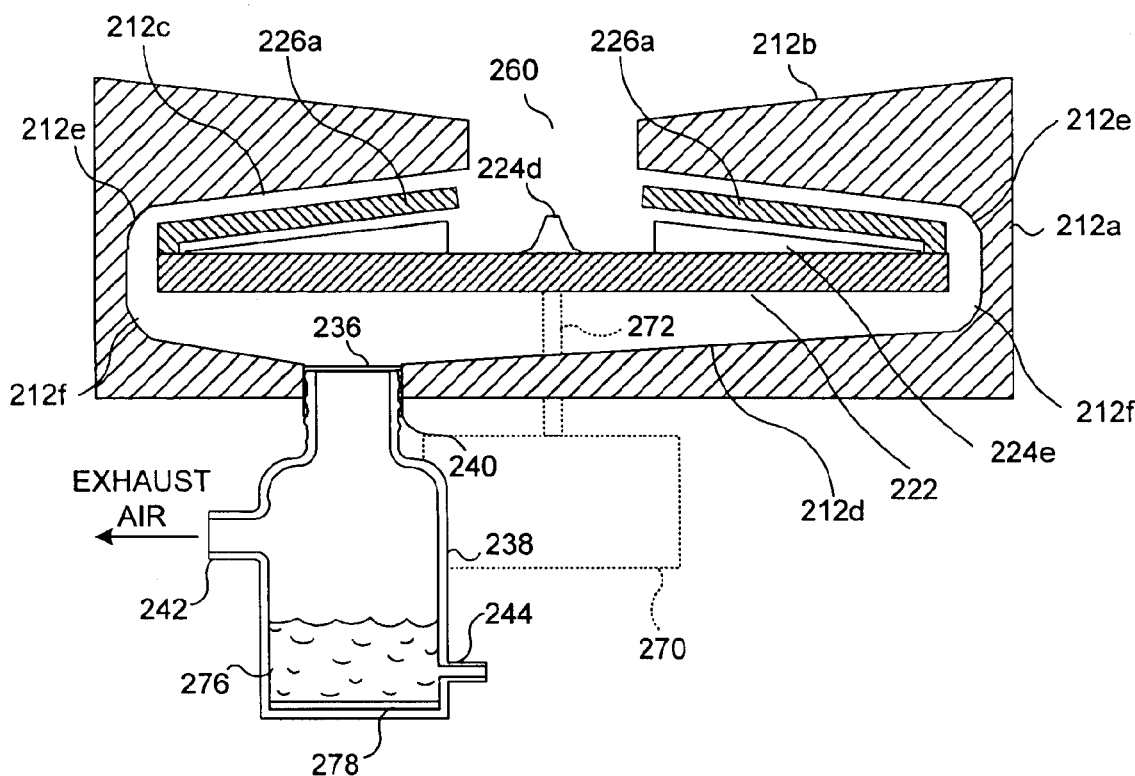

FIG. 15 schematically illustrates a particle collector including an impeller with vanes modified to enhance their performance in accord with the present invention; and FIG. 16 schematically illustrates performance enhancements made to the particle impactor of FIG. 13.

DESCRIPTION OF THE PREFERRED EMBODIMENT

Overview

The present invention relates to optimizing the configuration of a rotary impact collector. As will be described in greater detail below, such rotary impact collectors are useful in devices configured to collect particulates entrained in a gas, such as air sampling devices. Several such devices will be described in detail. Following a description of devices including rotary impact collectors, parameters for optimizing the performance of such collectors will be described. Those readers wishing to skip the description of devices that can beneficially include rotary impact collects and go directly to the discussion on optimizing rotary impact collectors can proceed immediately to the section entitled "Preferred Geometrical and Elemental Aspects of a Rotating Arm Collector".

Devices Incorporating Rotary Impact Collectors

A rotary impact collector can be beneficially employed as a combined particle impact collector and fan to both drive a gaseous fluid into a collection unit and to collect particulates. The combined particle impact collector and fan is readily fabricated in a sufficiently small size so as to enable it to be used in a portable collecting device that has the ability to process relatively large volumes of gaseous fluids in order to detect trace levels of contaminants. Several different embodiments are described below, including a collector in which the combined particle impact collector and fan is a disposable component and intended to be replaced after each use, as well as units in which the combined particle impact collector and fan is an integral component and adapted to be decontaminated and reused. A primary application of these collector devices is in monitoring ambient air to detect trace particulates and aerosols. Samples of particulates that are thus collected can be taken to offsite laboratories for analysis, or detection units can be integrated into the collection units for detecting specific substances in real time. The substances that are thus detectable may encompass a broad range of chemical and/or biological substances. For example, in accord with the present invention, chemical warfare agents or pathogens can be collected and identified by a field portable collector that includes an appropriate detection unit and is sufficiently small to be readily carried about by one person.

Personal Air-Monitoring Embodiment

Figure 1:
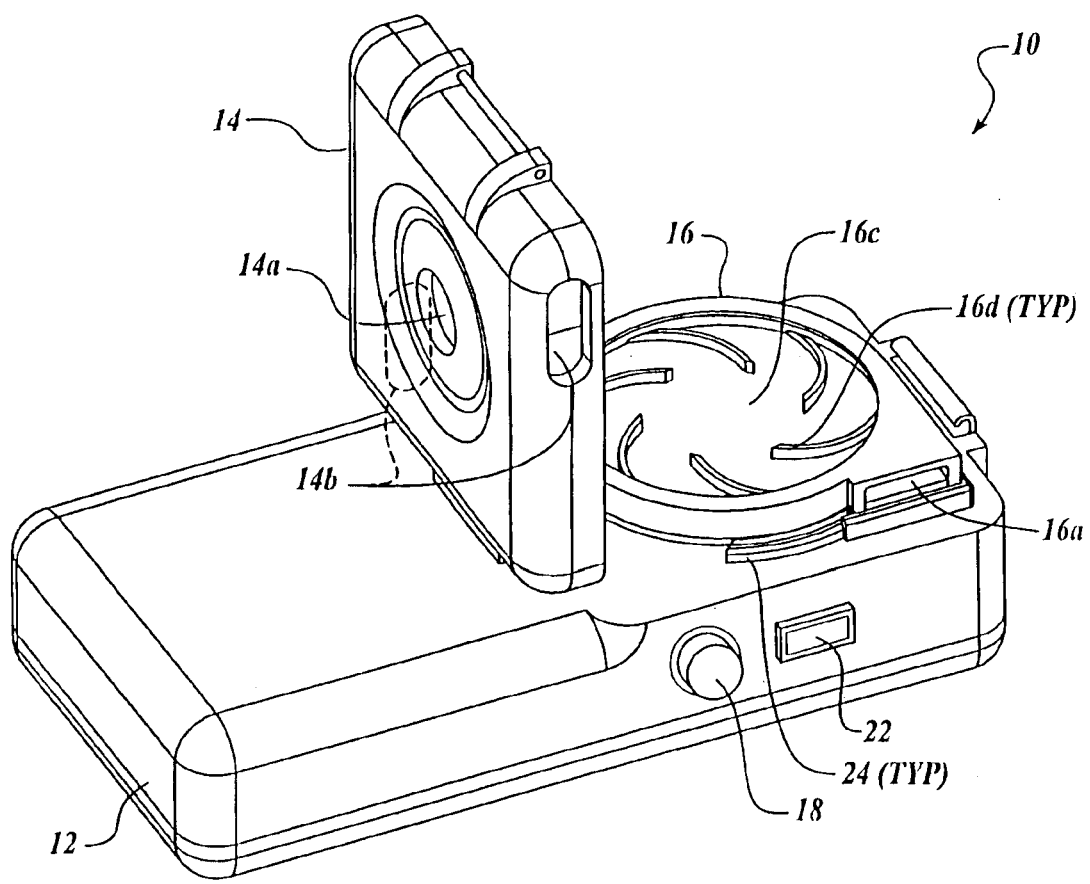
FIG. 1 is an isometric view of a portable sampler in accord with a first embodiment of the present invention.

A first embodiment of the present invention is illustrated in FIG. 1, which shows a functional prototype of a personal air-monitoring unit 10. It is anticipated that such a unit will fulfill a military requirement to assess an individual's potential exposure to harmful chemical and biological substances encountered in combat or as a result of terrorist activities. It should be noted however, that such a personal air-monitoring unit is expected to have wide spread application outside of military and law enforcement uses. For example, personal air-monitoring unit 10 might be used in hospitals, research facilities, and industrial facilities to detect exposure to dangerous substances that might be released into the environment due to accident. As potential exposure to airborne chemicals and biological organisms is relatively pervasive, it is contemplated that personal air-monitoring unit 10 will have widespread utility.

Personal air-monitoring unit 10 includes a primary housing 12, a secondary housing 14, a power switch 18, a battery charge indicator 22, and a disposable sample collection cartridge 16. Note that primary housing 12 includes a plurality of surface features 24 that help to correctly position disposable sample collection cartridge 16 on the primary housing. Secondary housing 14 includes an inlet air port 14a and an outlet air ports 14b. Inlet air port 14a overlies the center of a combined impact collector and fan 16c, while outlet air ports 14b correspond to outlet air ports 16a and 16b (see FIG. 2) on disposable sample collection cartridge 16. Combined impact collector and fan 16c (as configured in this embodiment) rotates in a clockwise direction, as viewed from above, and includes a plurality of arcuate vanes 16d that serve as impellers and provide rotating impact surfaces that collect particulates entrained within the air. Note that the direction of rotation is not critical, and that combined impact collector and fan 16c can also be rotated in a counterclockwise direction. As the combined impact collector fan rotates, typically at speeds in excess of 5,000 RPM, it draws ambient air through inlet air port 14a so that particulates can be separated from the air by impact with the surfaces of arcuate vanes 16d. It should be noted that the orientation of the outlet air ports 16a and 16b directs the exhaust air from which most of the particulates have been removed, to the sides of the unit.

Personal air-monitoring unit 10 is lightweight and designed to be worn by an individual for the purpose of monitoring the person's exposure to biological pathogens, or other airborne toxic particulates. Preferably, personal air-monitoring unit 10 is energized with a battery power supply and is sufficiently small in size and weight so as to minimize any inconvenience to the wearer. Power switch 18 can be selectively activated during a period of interest (such as while working in an area of potential contamination, or during a specific activity, such as while working with potentially ill patients, or in other areas where air quality or contamination is a concern). The personal air-monitoring unit can be de-energized to conserve battery life, when the wearer is no longer in an area of concern. Battery charge indicator 22 is included to warn a user of a low battery charge condition. It is contemplated that disposable or rechargeable batteries can be employed. While not specifically shown, it is contemplated that primary housing 12 will include mounting clips, to enable a user to mount personal air-monitoring unit 10 to a belt (or to clothing, a strap, or harness), much in the way a pager or other portable device is mounted. Such attachment might be completed with a clip, a buckled strap, a hoop/loop fastening strip, or other suitable fixtures, depending on a specific user's requirements. A functional prototype of the personal air-monitoring unit having an overall size of 4.5"×2.5"×1.3" has been developed. The overall weight of the functional prototype is less than 350 grams, and the weight of disposable sample collection cartridge 16 is less than 20 grams.

A different disposable sample collection cartridge 16 is needed for each sampling period. As will be described in detail below, the combined impact collector and fan is contained within each disposable sample collection cartridge. It is contemplated that each disposable sample collection cartridge will have a unique identifier (such as a barcode or RF tag—not shown), which specifically identifies each user. Preferably, once used, the disposable sample collection cartridge will be sealed in sterile packaging until opened for analysis. When the desired collection period has been completed (at the end of a work day, for example), the disposable sample collection cartridge is removed from personal air-monitoring unit 10 and is subjected to an analysis to detect biological or chemically hazardous particulates that may have been collected therein.

As will be discussed more in detail below, to facilitate analysis, a liquid sample must be obtained that includes particulates collected on the surfaces of arcuate vanes 16d. Thus, the disposable sample collection cartridge must be rinsed under controlled conditions to provide the liquid sample used in the analysis. The resulting particulate-laden rinse fluid will then be analyzed, and the sample collection cartridge safely discarded. The results, including information from the barcode (lot number, user, etc.) will preferably be displayed, documented, and transferred to a database for archival storage. With insertion of a new disposable cartridge and fresh batteries, the personal air-monitoring unit is ready to collect a new sample. Use of a disposable cartridge has the advantage of avoiding sample cross contamination without cumbersome decontamination procedures. A disposable also eliminates concerns of damage or reduced sample collection effectiveness that can be caused by decontamination procedures.

Figure 2:
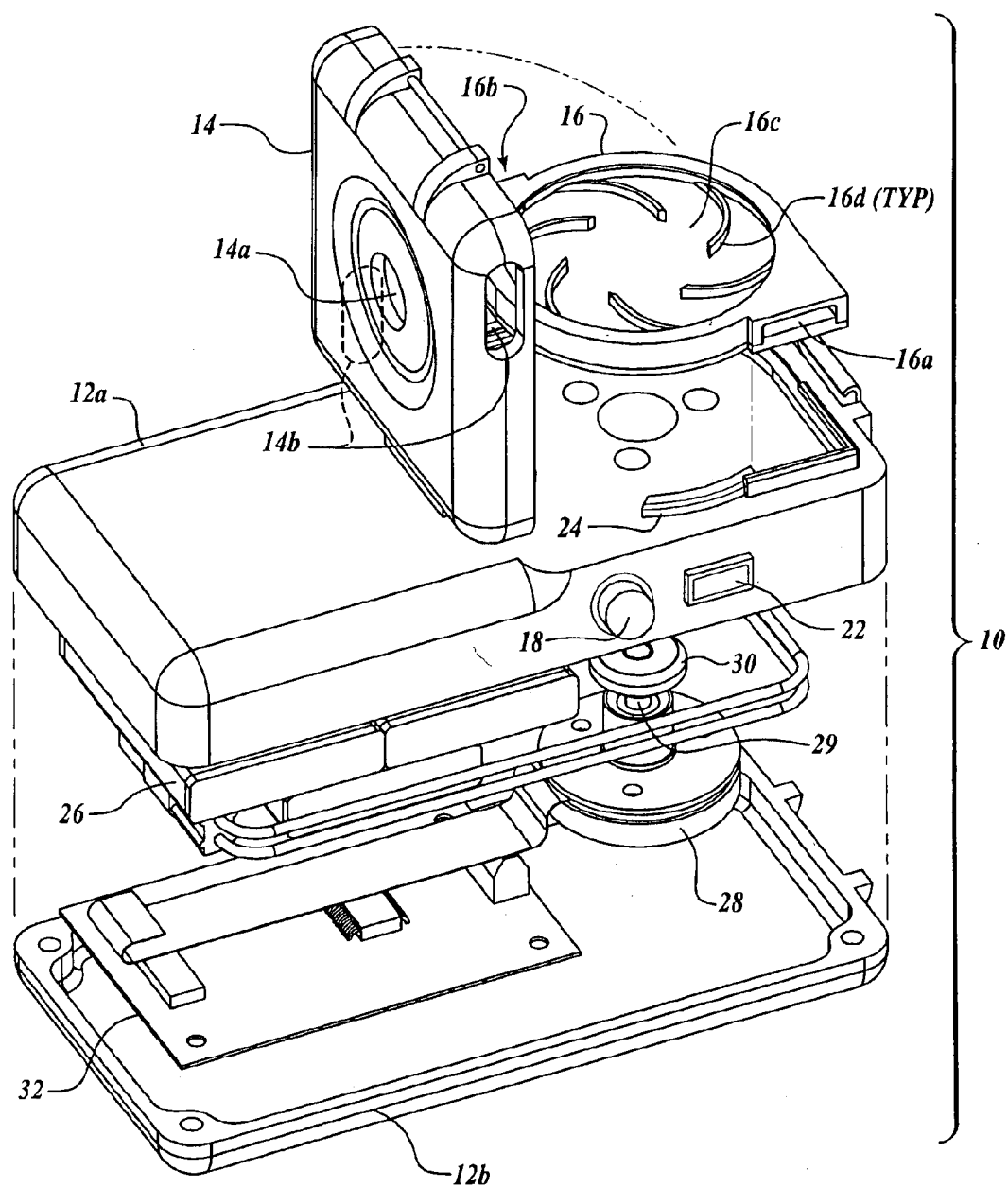
FIG. 2 is an exploded isometric view of the embodiment of FIG. 1.

Referring now to the exploded view in FIG. 2, additional details of personal air-monitoring unit 10 are visible. Primary housing 12 includes an upper section 12a and a lower section 12b. These housing sections are preferably removably connected together so that internal components can be changed when required (for example, to replace disposable batteries). Batteries 26 (rechargeable or disposable) energize an electric motor 28. Preferably, batteries 26 are lithium ion or metal hydride batteries, and electric motor 28 is a brushless, direct current type. Battery tests with the prototype unit discussed above have indicated that to achieve a uniform performance of the device over at least eight hours of continuous use, alkaline batteries are inadequate due to a significant voltage drop that occurs as such batteries discharge.

A drive shaft 29 terminates in a magnetic coupler 30. Magnetic coupler 30 is magnetically coupled to a ferromagnetic element (see FIG. 3B) included in combined impact collector and fan 16c. This magnetic coupling enables disposable sample collection cartridge 16 to be readily removed and replaced with a new cartridge, and enables combined impact collector and fan 16c to be drivingly coupled to drive shaft 29.

An electronic controller 32 is electrically coupled to power switch 18, battery charge indicator 22, batteries 26, and electric motor 28. Empirical data indicates that the rotational speed of electric motor 28 has a substantial effect on the collection efficiency of combined impact collector and fan 16c. Electronic controller 32 controls electric motor 28 so as to optimize collection efficiency and battery life. Furthermore, it is anticipated that additional empirical data will indicate a relationship between specific particulates and the optimal rotational speed for combined impact collector and fan 16c. As more details concerning this relationship are determined, electronic controller 32 will preferably be programmed to maintain different optimum speed ranges for a variety of different particulates, such that when desired, personal air-monitoring unit 10 can be optimized for collecting a specific particulate of interest.

Figure 3A:
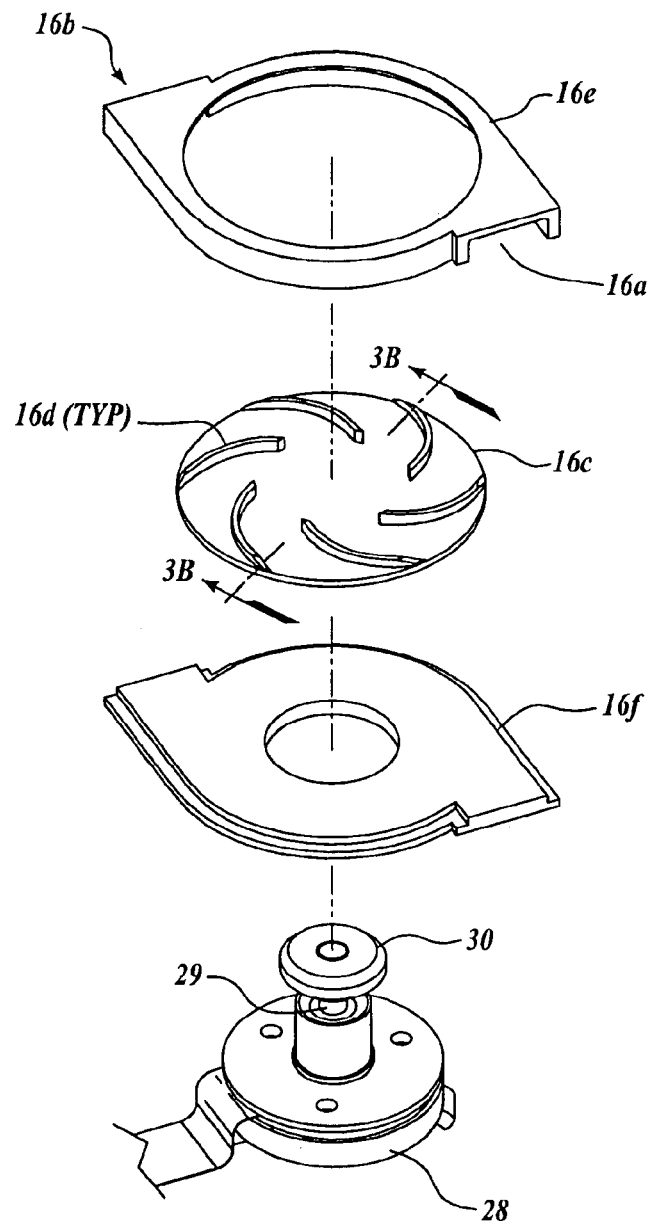
FIG. 3A is an exploded isometric view of a disposable sampling cartridge for use in the embodiment of FIG. 1.

FIG. 3A provides a more detailed view of the components of disposable sample collection cartridge 16, and shows how combined impact collector and fan 16 is coupled to drive shaft 29. Disposable sample collection cartridge 16 comprises an upper shell 16e, a lower shell 16f, and combined impact collector and fan 16c, which is disposed between the upper and lower shells. Note that when assembled, upper shell 16e and lower shell 16f form a fluid passage having outlet air ports 16a and 16b. As combined impact collector and fan 16c is rotated by electric motor 28 (via drive shaft 29 and magnetic coupler 30), particulate-laden air is drawn into the central opening formed in upper shell 16e, so that the particulates entrained in the air impact on and adhere to arcuate vanes 16d, until removed by rinsing.

Figure 3B:
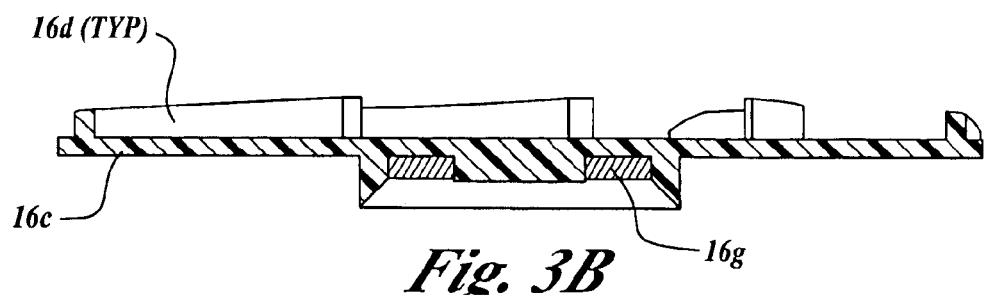
FIG. 3B is a cross-sectional view of a combined impact collector and fan, taken along line 3B—3B of FIG. 3A.

As shown in FIG. 3B and noted above, combined impact collector and fan 16c includes a ferromagnetic element 16g, which is magnetically coupled to magnetic coupler 30. Preferably, ferromagnetic element 16g is of a relatively low mass, so that it imposes very little additional load on electric motor 28; the smallest mass ferromagnetic element capable of ensuring positive magnetic coupling is employed. Of course, ferromagnetic element 16g must be carefully placed in the center of the combined impact collector and fan 16c so that rotation efficiency of combined impact collector and fan 16c is not adversely affected. Note that a ferromagnetic element 16g that is too massive will likely negatively affect battery life expectancy. In the prototype collector unit, a small iron washer was effectively employed for ferromagnetic element 16g.

Preferably upper shell 16e, lower shell 16f, and combined impact collector and fan 16c are fabricated from a plastic material. It is anticipated that injection molded components of suitable quality can be inexpensively produced in large quantities. Preferably, lower shell 16f and/or combined impact collector and fan 16c are fabricated from a plastic material that exhibits good self lubricating properties so that neither bearings nor additional lubricants are required to enable combined impact collector and fan 16c to freely rotate between the upper and lower shells.

Once disposable sample collection cartridge 16 has been collecting particulates for a desired period of time, the particulates need to be removed from combined impact collector and fan 16c for analysis. Preferably, a liquid sample that includes particulates, which were collected on the internal surfaces of the sample collection cartridge, will be prepared, as most analytical techniques are adapted to process liquid samples. While many techniques are known for preparing a liquid sample, the present invention preferably employs a rinse station specifically designed to prepare a liquid sample from a disposable sample collection cartridge 16.

In the most generic embodiment, the rinse station will use a known volume of rinse solution to extract a liquid sample from a disposable sample collection cartridge 16. To enhance rinsing, a wetting agent or surfactant can optionally be added to the rinse solution. It is anticipated that a heated rinse fluid will be particularly useful in cold environments. As the rinse station is to be field portable, it is likely that the rinse station will be employed in unheated conditions in cold climates. If the analytical technique to be employed is based on culturing biological organisms, then a rinse solution that is non-toxic to such organisms must be employed. Preferably, a phosphate buffer rinse solution will be used when applying such culturing techniques. Other contemplated rinsing enhancements that can be incorporated into the rinse station in accord with the present invention include an ultrasonic transducer that applies an ultrasonic pulse to the disposable sample collection cartridge during rinsing, or a vibration unit that vibrates the disposable sample collection cartridge during rinsing, or an electric motor that rotates the combined impact collector and fan in the disposable sample collection cartridge during rinsing. The vibration unit is discussed in greater detail below.

Figure 4A:
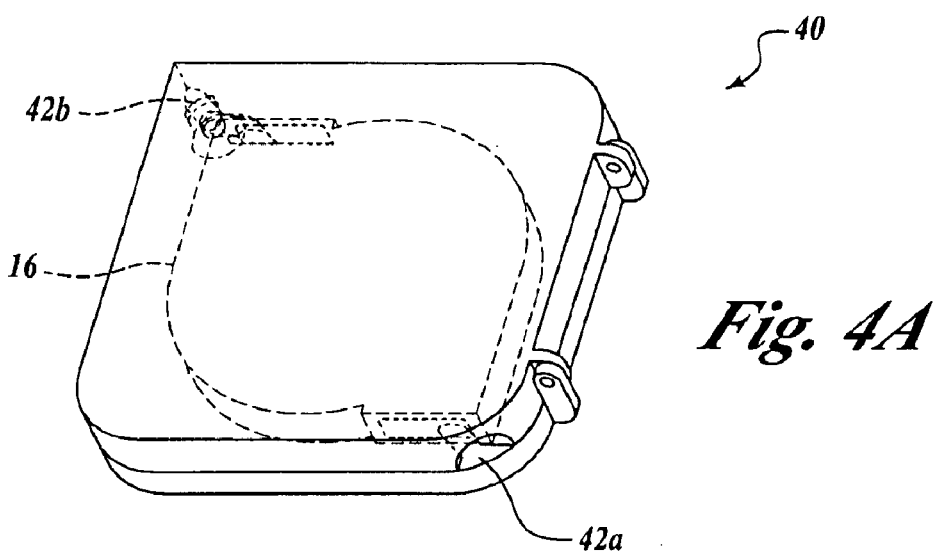
FIG. 4A is an isometric view of a disposable rinse cassette employed when extracting a sample from the sampling cartridge of FIG. 3A.
Figure 4B:
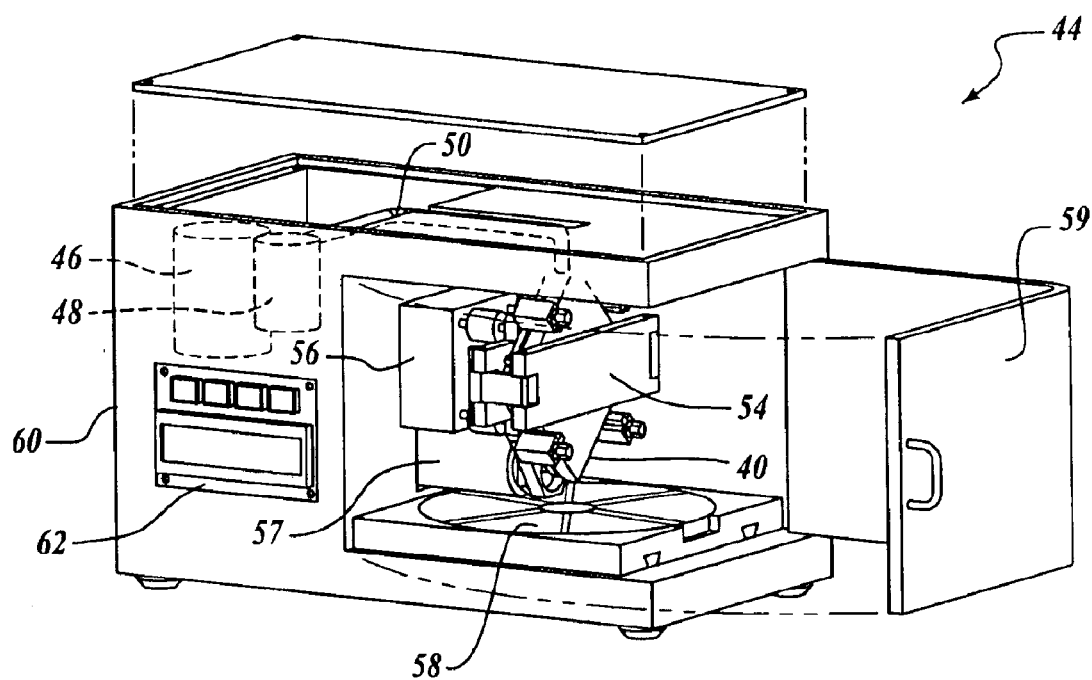
FIG. 4B is an isometric view of a preferred embodiment of a rinse station employed to extract a sample from a sampling cartridge that is inserted into the rinse cassette of FIG. 4A.

FIGS. 4A and 4B illustrate elements of a preferred rinsing station. In FIG. 4A, a rinse cassette 40 is shown, with a disposable sample collection cartridge 16 held inside the rinse cassette. Preferably an interior surface of rinse cassette 40 is contoured to approximately match the shape of disposable sample collection cartridge 16, thereby minimizing a volume of rinse fluid that will be injected into rinse cassette 40 during rinsing. Rinse cassette 40 includes a fluid port 42a through which the rinse fluid is injected into rinse cassette 40, and a fluid port 42b that includes an integral pinch valve. When the pinch valve is actuated after the rinsing step is complete, a sample of the rinse fluid containing particulates that have been rinsed from combined impact collector and fan 16c is removed from rinse cassette 40.

After the disposable sample collection cartridge 16 is inserted into rinse cassette 40, the rinse cassette is then inserted into a rinse station 44, illustrated in FIG. 4B. Rinse station 44 includes a rinse fluid reservoir 46, a fluid pump 48 that enables a precisely metered volume of rinse fluid to be injected into the rinse cassette, and a fluid line 50 is in fluid communication with fluid pump 48, rinse fluid reservoir 46, and rinse cassette 40 that is held in place by a bracket 54. Note that when rinse cassette 40 is properly positioned and latched in place by bracket 54, fluid port 42a of rinse cassette 40 is in fluid communication with fluid line 50. Thus, a precisely metered volume of rinse fluid can be injected into rinse cassette 40. Because the pinch valve associated with fluid port 42b is not actuated, rinse fluid injected into rinse cassette 40 will be retained within the rinse cassette until a sample is withdrawn by actuating the pinch valve.

Rinse station 44 also includes a vibration unit 56. When a rinse cassette has been placed into rinse cassette bracket 54 and filled with a precisely metered volume of fluid, vibration unit 56 is energized to vibrate the combined impact collector and fan disposed within rinse cassette 40. This vibration aids in removing adhered particulates from the surfaces of the combined impact collector and fan. It is contemplated that an ultrasonic transducer unit can alternatively replace vibration unit 56 to provide ultrasonic pulses that loosen the particulates from the surfaces of the collector.

Note that when a rinse cassette is properly positioned and held in place by bracket 54, fluid port 42b and its pinch valve are disposed immediately adjacent to a solenoid unit 57. Once the rinse cycle is complete, solenoid unit 52 is energized, and the pinch valve associated with fluid port 42b is actuated. Fluid port 42b of rinse cassette 40 is disposed immediately above a lateral flow disk 58. The rinse liquid injected into rinse cassette (carrying particulates removed from the combined impact collector) drains onto the lateral flow disk, where it is collected for analysis. It is anticipated that another type of sample collector, such as a vial or ampoule (not shown), will be placed under fluid port 42b to collect the sample.

Finally, rinse station 44 includes a housing 60 that substantially encloses rinse fluid reservoir 46. Pump 48 and solenoid unit 57 are also enclosed by housing 60, and lateral flow disk 58 and rinse cassette bracket 54 are enclosed by a removable screen or door 59. A control panel 62 enables a user to control pump 48, vibration unit 56, and solenoid unit 57 during the rinse cycle.

It should be noted that alternative embodiments of rinse cassette 40 and rinse station 44 are contemplated. It may be desirable to enable a sealed rinse cassette or the combined impact collector and fan to be rotated by an electric motor (not separately shown) during the rinse cycle, to further aid in the removal of attached particulates. Rinse cassette 40 could not be rotated in this fashion, as the rinse fluid would leak out of fluid port 42*a* during the rotation. A pinch valve (not separately shown) could be included in fluid port 42*a*, so that rinse fluid cannot enter or exit the rinse cassette unless the pinch valve is actuated. This modification would require either an additional solenoid (also not shown) to be included in rinse station 44 to actuate the added pinch valve associated with fluid port 42*a*. Alternatively, a fluid line in fluid communication with fluid port 42*b*, pump 48, and rinse fluid reservoir 46 could be added to rinse station 44, so that fluid port 42*b* would be used to both fill and drain the rinse cassette, eliminating the need for fluid port 42*a*, or an additional solenoid unit and pinch valve.

To minimize the volume of reagents required, and to minimize the amount of waste generated, it is preferred that small volumes of rinse fluid be employed. It is anticipated that 1–5 ml of rinse fluid represents a preferred range. However, it should be understood that more or less rinse fluid can be employed, depending on the nature of the particulates collected, the size of the disposable sample collection cartridge, and other factors. FIG. 5 illustrates a personal air-monitoring unit 10*a*. This embodiment incorporates a detection unit 64, which is capable of identifying a specific particulate of interest. Detection unit 64 is intended to be disposable and to be replaced at the same time as disposable sample collection cartridge 16, following its use in attempting to detect substances in the sample that was collected by the personal air-monitoring unit.

Note that detection unit 64 will be specifically designed to detect a particular chemical or microorganism (or a class of chemicals or pathogens), and will not be sensitive to non-target agents. Thus, if anthrax spores have been collected, but detection unit 64 is designed to detect nerve gas agents, the presence of anthrax will not be reported. While it would be preferable for detection unit 64 to be capable of detecting all types of particulates of interest, i.e., all chemical/biologically harmful agents, the state of the art of detection technology is not yet capable of implementing such a wide spectrum detector in a size that can be included in a portable and disposable detector. However, the state of the art of detection technology does offer a wide variety of detectors for specific substances that can be employed as compact and disposable units. These detectors can be fabricated to detect a specific substance or class of substances from a wide variety of different target substances. Preferably, detection unit 64 is adapted to detect at least either a chemical, a biological pathogen, a biological toxin, an allergen, a mold, or a fungi.

Preferably, detection unit 64 is configured in an elongate, relatively thin card shape and includes a plurality of micro-fluidic channels. Detection unit 64 will include all the reagents required to perform the desired analysis. The use of micro-fluidic architecture enables relatively small quantities of reagents to detect a substance in a relatively small amount of a sample, so that a compact detection system is readily implementable.

Such card based detection units have been developed by Micronics, Inc., based in Redmond, Wash. Micronics has developed several lab-on-a-chip technologies that are implemented as low-cost plastic, disposable, integrated micro-fluidic circuits, typically in credit card-sized cartridges. These micro-fluidic channels were originally developed using microfabrication techniques established within the semiconductor manufacturing industry. Micro-fluidic channels, on the order of hundreds of microns in diameter, are now easily fabricated on silicon chips and other substrates. Fluids flowing in these small channels have unique characteristics that can be applied to different detection methodologies, including cell and separation without centrifugation or filtration. The miniaturization of these processes ensures that minimal volumes of reagents will be needed, minimal volumes of sample will be required, and minimal volumes of waste will be generated.

These micro-fluidic systems are ideal for detecting a substance in the same instrument in which a sample has been collected, eliminating the need to transport the sample to a centralized laboratory, and providing immediate or real time results. The O.R.C.A. µFluidics™ product line of Micronics, Inc. is particularly well suited for use with personal air-monitoring unit 10a. The card-based detection system used in this product usually includes a standard sample input port, one or more reagent introduction ports (not shown), sample storage structures, and waste compartments, and may also contain various micro-fluidic separation and detection channels, incubation areas, micro-fluidic reactors, and valves, details of which are not specifically illustrated.

Figure 5:
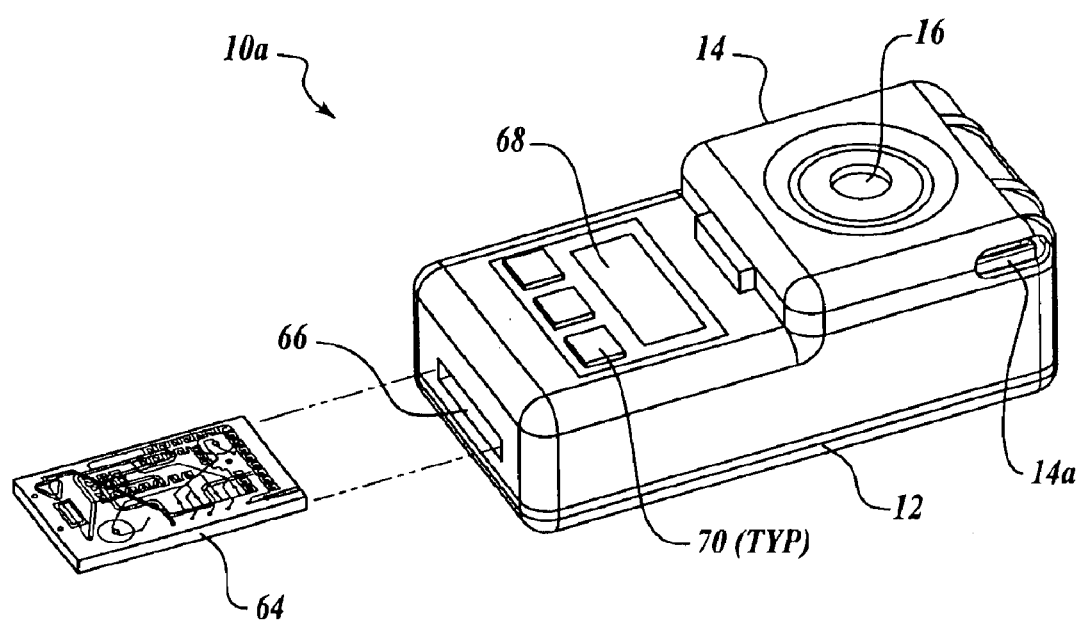
FIG. 5 is an isometric view of a portable sampler and integrated sensor unit in accord with a second embodiment of the present invention.

With respect to FIG. 5, detection unit 64 is exemplary of the O.R.C.A. µFluidics™ product line. It should be noted that the specific internal layout of a detection unit adapted to detect nerve gas might be quite different than that of a detection unit intended to detect another type of chemical or biological agent, and the internal design of detection unit 64 is for illustrative purposes only. Regardless of the specific internal design used in the detection unit, each different type of detection unit will include standard interface port to enable samples to be introduced into the detection unit, as well as to enable a result to be displayed. It is anticipated that when the target particulate is a biological organism or pathogen, flow cytometry (the counting and characterization of biological cells) will be a preferred detection methodology employed in detection unit 64. It is further anticipated that immuno assay and nucleic acid base detection methods can be employed in a micro-fluidic or other portable and disposable detection unit.

Referring once again to FIG. 5, detection unit 64 is inserted into a slot 66 in primary housing 12. Preferably slot 66 is disposed above the batteries inside primary housing 12, although the specific disposition of the slot is not critical. A display 68 is provided on personal air-monitoring unit 10a so that the result of the analysis and detection process carried out by detection unit 64 is displayed to a user. A plurality of controls 70 are further provided to enable a user to activate detection unit 64 after a desired sampling period has been completed. It is also contemplated that display 68 could be incorporated onto detection unit 64, although such an embodiment would likely increase the cost of each disposable detection unit 64. While not separately shown, it should be understood that disposable sample collection cartridge 16 will include a fluid port through which the rinse fluid that has removed particulates from combined impact collector and fan 16c will flow. Furthermore, personal air-monitoring unit 10a includes fluid lines (not shown) that enable detection unit 64 to be connected to disposable sample collection cartridge 16 to receive the liquid sample in sample input port 65 of detection unit 64.

It should be noted that portable sampling units incorporating combined impact collectors and fans in accord with the present invention could be integrated with other types of detector units. The micro-fluid based detectors discussed above are merely exemplary, and should not be considered limiting on the present invention. Other suitable detection units are likely to include color change based test strips, such as those available from Tetracore, Inc. (Gaithersburg, Md.) for determining the presence of anthrax, and sensor-on-a-chip technologies that are available from a number of different companies (for example, such devices can be found on the taosinc.com website). It is anticipated that immunoassay based detection systems, such as cytometry and fluorescence based systems, and nucleic acid based detection systems will be particularly useful.

Portable Area Air-Monitoring Embodiment

FIGS. 6A, 6B, 7, 8A, 8B, and 9 illustrate aspects of air-monitoring units 100 and 100a that are also portable, but are more rugged than personal air-monitoring units 10 and 10a. These more rugged air-monitoring units 100 and 100a are designed to be extremely durable, and are particularly well suited to be used in emergency response situations by fire fighters and personnel responding to incidents in which potentially hazardous materials may have been released into the environment. While air-monitoring units 100 are 100a is are functionally similar to personal air-monitoring units 10 and 10a in that they all include a combined impact collector and fan, the combined impact collector and fan elements in the more rugged air-monitoring units are designed to be permanent components rather than disposables. These larger, more rugged air-monitoring units include appropriate valves, fluid lines and a pump (note that these elements were incorporated into the rinse station used in connection with the smaller personal air-monitoring unit 10 described above). These units are particularly well suited to obtain samples from areas containing suspected hazards, such as rooms or vehicles. A disposable fluid cartridge 120 used with air-monitoring unit 100 provides a rinse fluid, as well as a rinse fluid reservoir 122a for the sample collected when the combined impact collector and fan is rinsed. Because the combined impact collector and fan is continually reused, the disposable fluid cartridge preferably includes a decontaminating solution as well, so that the combined impact collector and fan, as well as the internal fluid lines, can be cleaned after or before each successive sample is collected.

Figure 6A:
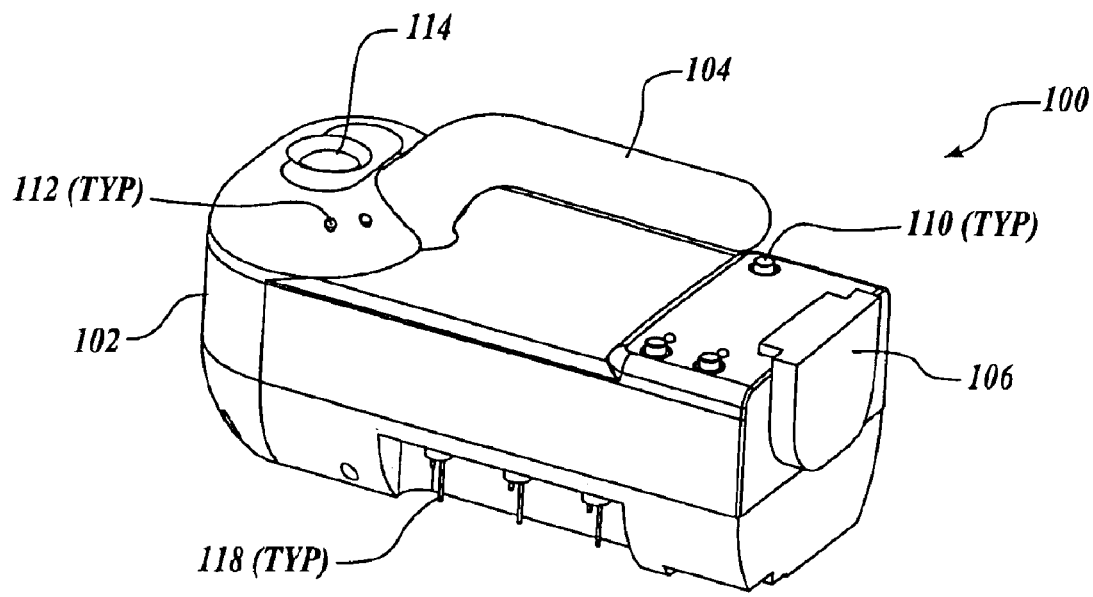
FIG. 6A is an isometric view of a portable sampler unit in accord with another embodiment of the present invention.

Referring now to FIG. 6A, air-monitoring unit 100 includes a rugged, high impact and waterproof housing 102 that encloses all of the components of the air-monitoring unit. Because this air-monitoring unit was designed to be used by fire fighters and other emergency response personnel, ruggedness and waterproof housing qualities were key functional design objectives. It should be understood that for other applications, a waterproof or extremely rugged housing might not be required. Housing 102 includes an integral handle 104. Note that the size and shape of handle 104 has been ergonomically chosen to accommodate the hand of a user wearing bulky protective gloves. While not shown, a plurality of attachment points are preferably included in housing 102 to enable a variety of different carrying straps to be used transporting air-monitoring unit 100. Despite its relatively small size, its robust construction results in a surprisingly heavy unit, so carrying straps are quite useful.

Air-monitoring unit 100 is designed to be energized by rechargeable batteries. A battery access cover 106 enables batteries to be changed as required. While many types of batteries can be employed, air-monitoring unit 100 has been specifically designed to use lead acid rechargeable batteries that are commonly used to energize professional quality audio-visual equipment. These batteries are readily available, extremely durable, and can be charged and discharged many times before they need to be replaced.

A plurality of user activatable controls 110 are provided. Preferably these controls comprise waterproof switches that require a significant amount of force to actuate, to prevent accidental activation of the controls. As noted above, it is anticipated that users will frequently be wearing bulky protective gloves, so sufficient space is provided between the controls to enable any control to be actuated without accidentally actuating an adjacent control. Of the three control switches shown, preferably one energizes the unit, a second control switch executes a decontamination cycle, and a third control switch initiates a sample collection. A plurality of indicator lights 112 are also provided. Preferably, one indicator light verifies that the unit is energized, and a second indicator light alerts a user if an operational error is detected.

The combined impact collector and fan included in air-monitoring unit 100 cannot be seen in the external view. A fluid inlet 114 enables particulate-laden air to enter the unit. A fluid outlet (not visible in the view of FIG. 6A) is also provided at the front of the unit, to enable sampled air to escape after most of the particulates have been removed.

Figure 6B:
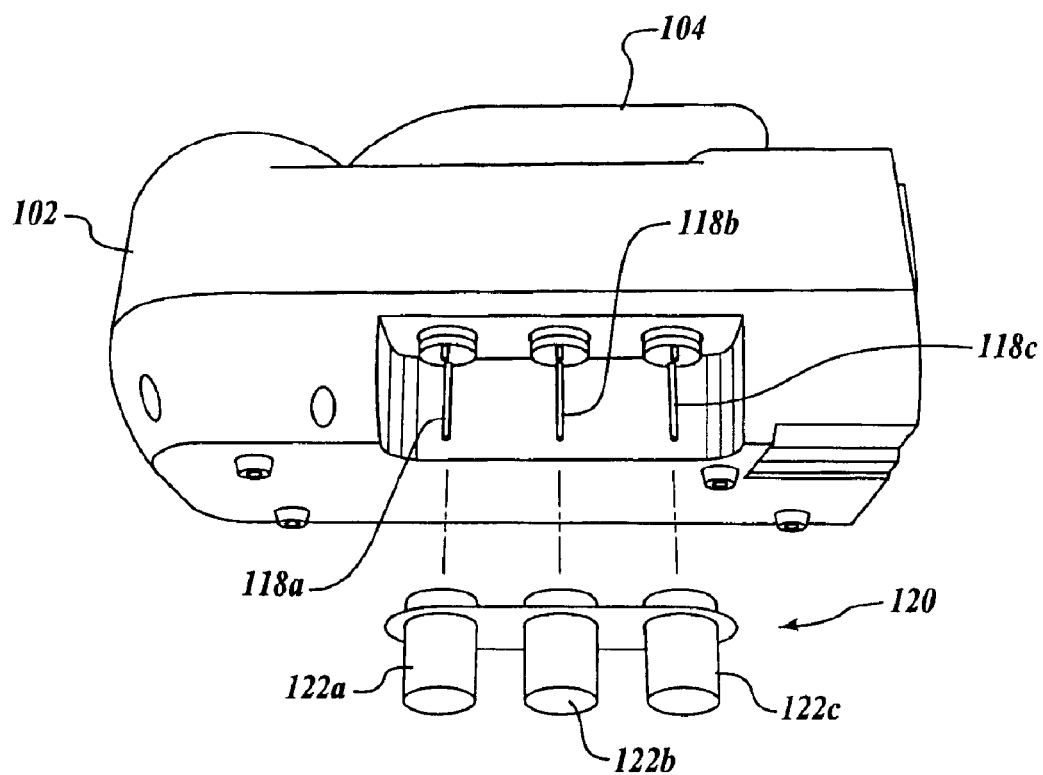
FIG. 6B is a modified side view of the portable sampler unit of FIG. 6A, also showing a removable sample cartridge that is used with the unit.

A plurality of fluid tubes or ports 118 are disposed on the left side of air-monitoring unit 100. These fluid ports convey the rinse fluid, decontamination fluid, and particulate-laden rinsate, which is collected in a disposable fluid cartridge. FIG. 6B provides a clearer view of fluid ports 118, as well as disposable fluid cartridge 120. A rinse fluid port 118b is in fluid communication with rinse fluid reservoir 122b when disposable fluid cartridge 120 is properly coupled to air-monitoring unit 100. A plurality of elastomeric sealing surfaces are disposed adjacent to fluid ports 118, to enable disposable fluid cartridge 120 to securely couple to air-monitoring unit 100 without leaking any fluid from the reservoirs.

Preferably the rinse fluid includes a wetting agent to reduce liquid surface tension of the rinse fluid and to increase the effectiveness of the rinse. As noted above, if a biological organism is the target particulate, and culturing will be employed as the detection method, then preferably, the rinse fluid used will not be toxic to the biological organism of interest. Phosphate buffer solutions are generally non-toxic to biological particulates and will typically be used in this case. Also as noted above with respect to the personal air monitoring embodiment, the use of a heated rinse fluid may be desirable in cold climates. Either a heater (not separately shown) can be incorporated into air-monitoring unit 100, or disposable fluid cartridge 120 can be warmed before use.

Once the combined impact collector and fan has been properly rinsed, the rinsate (including the particulates removed by the rinsing process) are delivered to a sample reservoir 122c in disposable fluid cartridge 120 via a fluid port 118c. Note that when disposable fluid cartridge 120 is initially coupled to air-monitoring unit 100, sample reservoir 122c is empty and will preferably be sterile.

Because the combined impact collector and fan of air-monitoring unit 100 is not disposable, it is preferable for the combined impact collector and fan, and any associated fluid lines, to be decontaminated in between sampling sessions, to avoid potential cross contamination of samples. When disposable fluid cartridge 120 is coupled to air-monitoring unit 100, fluid port 118a is in fluid communication with a decontamination fluid reservoir 122a. A biocidal fluid is preferably employed to decontaminate the system. For example, either a bleach solution or a hydrogen peroxide solution (the commonly available 3% solution is adequate) is utilized as a decontamination fluid. Other protein/nucleic acid decomposing fluids can be similarly employed. It is preferred that the decontamination process be carried out prior to a sample collection (to ensure no contaminants have been picked up during storage of air-monitoring unit 100); however, the decontamination process can instead be executed immediately after sample collection has been completed. Preferably, the biocidal decontamination fluid employed does not interfere with the desired analysis. For example, a peroxide based decontaminating fluid is incompatible with polymerase chain reaction (PCR) assay based detection techniques, and when PCR assay based detection techniques are to be carried out, a non peroxide based decontaminating solution should be utilized.

Alternatively, a first disposable fluid cartridge 120 can be specifically dedicated to rinsing and sampling, while a second disposable fluid cartridge 120 can be specifically dedicated to decontamination. In this scenario, a dedicated sampling fluid cartridge (not separately shown, but identical in appearance to disposable fluid cartridge 120) will have a first fluid reservoir filled with a sterile water solution for a first rinse that is executed prior to the sample collection to ensure that the combined impact collector and fan is clean prior to the sample collection. A second fluid reservoir will contain the rinsing fluid (for removing particulates collected during the sampling period), while a third fluid reservoir will be used for collecting the particulate laden rinsate (the sample). A dedicated decontamination fluid cartridge (also not separately shown, but also identical in appearance to disposable fluid cartridge 120) will have a first fluid reservoir filled with a decontamination fluid for a decontamination flush. A second fluid reservoir will contain a neutralizing solution, which deactivates or neutralizes any residual decontamination fluid. Finally, the third reservoir will contain a sterile water solution for a final rinse. The purpose of the neutralizing solution, and the final rinse, is to ensure that all the decontamination fluid is removed, so that a subsequently collected sample is not adversely affected by an incompatible decontamination fluid.

After air-monitoring unit 100 has rotated the combined impact collector and fan for a desired time period; and the rinsing and decontamination cycles have been completed, the spent disposable fluid cartridge is removed and replaced with a fresh cartridge. The sample contained in the sample reservoir is then delivered to a laboratory (or a field portable analytical station) for analysis. While not individually shown, each fluid reservoir in disposable fluid cartridge 120 preferably includes a leak-proof cap, so that fluids are not spilled when the disposable fluid cartridge is stored or being manipulated. Disposable fluid cartridge 120 is preferably fabricated from a plastic material.

Figure 7:
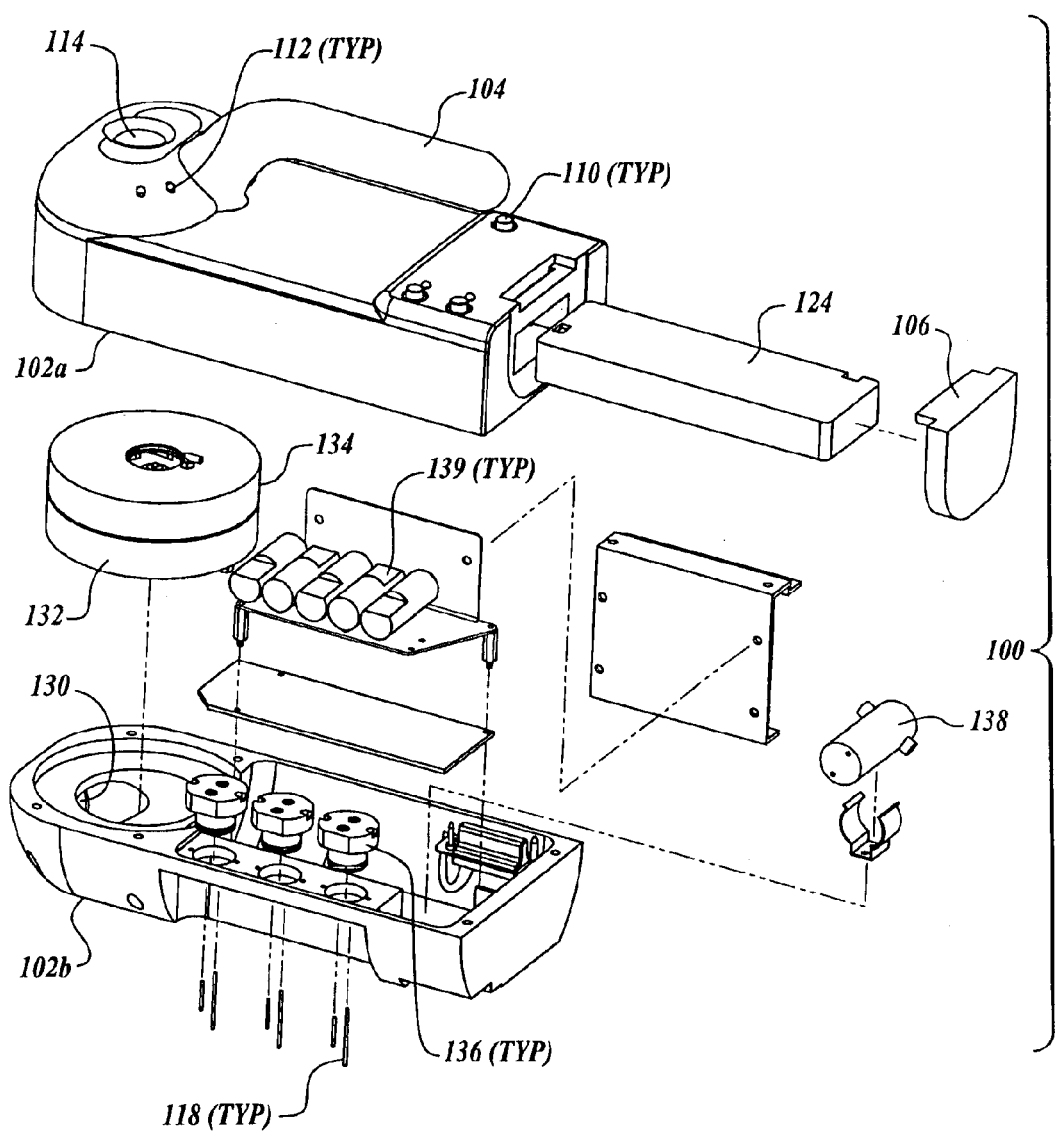
FIG. 7 is an exploded isometric view of the portable sampler unit of FIG. 6A.

FIG. 7 illustrates further details of air-monitoring unit 100. A rechargeable battery 124 is disposed in an upper housing 102a. Sandwiched between upper housing 102a and a lower housing 102b is a housing 132 in which is disposed a combined impact collector and fan 134 and an electric motor, which is not separately shown. While not specifically shown, it should be understood than the electric motor is electrically coupled to battery 124, and to controls 110 and rotatably drives the combined impact collector and fan to collect particulates, just as explained above in regard to personal air-monitoring units 10 and 10a.

Lower housing 102b includes a fluid outlet port 130 that enables air drawn into air-monitoring unit 100 via fluid inlet port 114 to be exhausted. A plurality of valves 139 and nozzle manifolds 136 are disposed in lower housing 102b, such that each fluid reservoir of disposable fluid cartridge 120 (see FIG. 6B) is serviced by a separate valve/nozzle combination. Each nozzle manifold 136 includes two nozzles, with a separate valve 139 serving each nozzle. The only exception to this is the valve/nozzle combination servicing fluid port 118b, which employs a single valve, rather than two valves. This difference arises because fluid port 118b is used for the rinse fluid inlet, and the rinse fluid is never reintroduced into rinse fluid reservoir 122b via fluid port 118b (as the spent rinse fluid is directed to sample reservoir 122c via fluid port 118c); consequently, a second valve is not required. Two valves are associated with decontamination fluid port 118a and sample fluid port 118c, such that a flow of fluid entering and exiting the unit in respect to decontamination fluid reservoir 122a and sample fluid reservoir 122c, can be independently controlled. One valve associated with the nozzle leading to decontamination fluid port 118a enables virgin decontamination fluid to enter air-monitoring unit 100, while a second valve associated with the same nozzle returns spent decontamination fluid to decontamination fluid reservoir 122a. One valve associated with the nozzle leading to sample fluid port 118c enables particulate laden rinse fluid to exit air-monitoring unit 100 and flow into sample reservoir 122c, while a second valve associated with the same nozzle enables the sample fluid to be reintroduced into air-monitoring unit 100, either to recycle the rinsate (for embodiments that continually rinse during sampling) or for analysis (i.e., for embodiments described below that incorporate integrated detection units). Preferably, valves 139 are pinch valves.

Also disposed in lower housing 102b is a fluid pump 138 that withdraws the rinse fluid from the rinse fluid reservoir of disposable fluid cartridge 120, and pumps the rinse fluid into combined impact collector and fan 134 to rinse particulates from the surfaces of the combined impact collector and fan. Pump 138 is also employed to pump decontamination fluid from the decontamination fluid reservoir in disposable fluid cartridge 120, applying the decontamination fluid to combined impact collector and fan 134, to decontaminate the unit between successive sampling cycles. Finally, pump 138 is employed to ensure that all rinse fluid used to rinse combined impact collector and fan 134 is transferred to sample reservoir 122c in disposable fluid cartridge 120. While not specifically shown, it should be understood that internal fluid lines are provided to couple combined impact collector and fan 134 in fluid communication with fluid ports 118. Combined impact collector and fan 134 is functionally identical, and structurally similar to combined impact collector and fan 16c of personal air-monitoring unit 10 and 10a. However, because combined impact collector and fan 134 is not required to be magnetically coupled to the electric motor that rotates it, it does not include any ferromagnetic element. Also, because combined impact collector and fan 134 is intended to be a permanent and integral component that will be frequently decontaminated, the material from which combined impact collector and fan 134 is fabricated must be able to endure such an extended life that can endure thousands of cycles. A preferred material for the combined impact collector is Altem™ or Teflon embedded Delrin™.

Figure 8A:
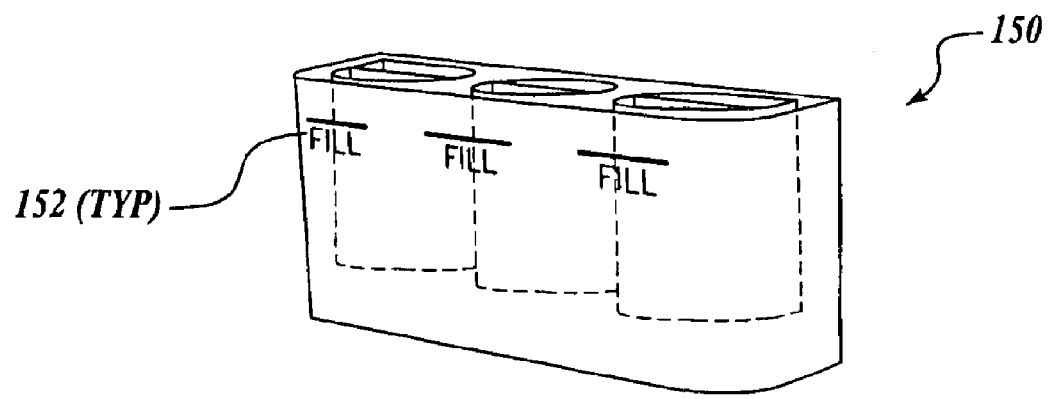
FIG. 8A is a front view of a diagnostic cartridge for use with the portable sampler unit of FIG. 6A.
Figure 8B:
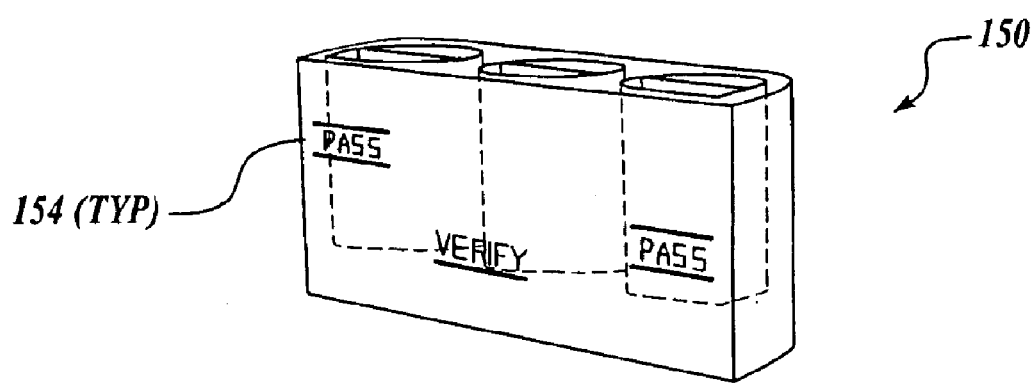
FIG. 8B is a rear view of a diagnostic cartridge for use with the portable sampler unit of FIG. 6A.

In addition to disposable fluid cartridges 120, a diagnostic cartridge 150 is preferably provided with air-monitoring unit 100. The diagnostic cartridge is shown in FIGS. 8A and 8B and its function is to serve as a tool that can be periodically used to ensure that the fluidic components of air-monitoring unit 100 are functioning properly. The principle embodied in diagnostic cartridge 150 is simple. A known volume of fluid is injected into air-monitoring unit 100 during a test rinse cycle. The volume of fluid captured after the completion of the rinse cycle is then measured to determine if any fluid loss is within acceptable limits. To use diagnostic cartridge 150, a user fills the cartridges corresponding to the disposition of rinse reservoir 122a and decontamination fluid reservoir 122b with a fluid (preferably sterile water, or a specialized cleaning fluid that includes surfactants) to a level indicated by fill lines 152. Note that one side of diagnostic cartridge 150 is marked with fill lines 152 (FIG. 8A), while the opposite side of diagnostic cartridge 150 is marked with a plurality of pass lines 154. Once diagnostic cartridge 150 is properly filled and inserted into air-monitoring unit 100 (in the same location and fashion that disposable fluid cartridge 120 is connected), the user initiates a test sampling cycle. At the end of the test sampling cycle, the user examiners the level of fluid returned to diagnostic cartridge 150 relative to pass lines 154. If the level of fluid is within the pass marks, the unit is functioning properly. If the fluid levels are not within the pass marks, this indicates that the unit is not functioning properly and that air-monitoring unit 100 should be removed from service until repaired.

Figure 9:
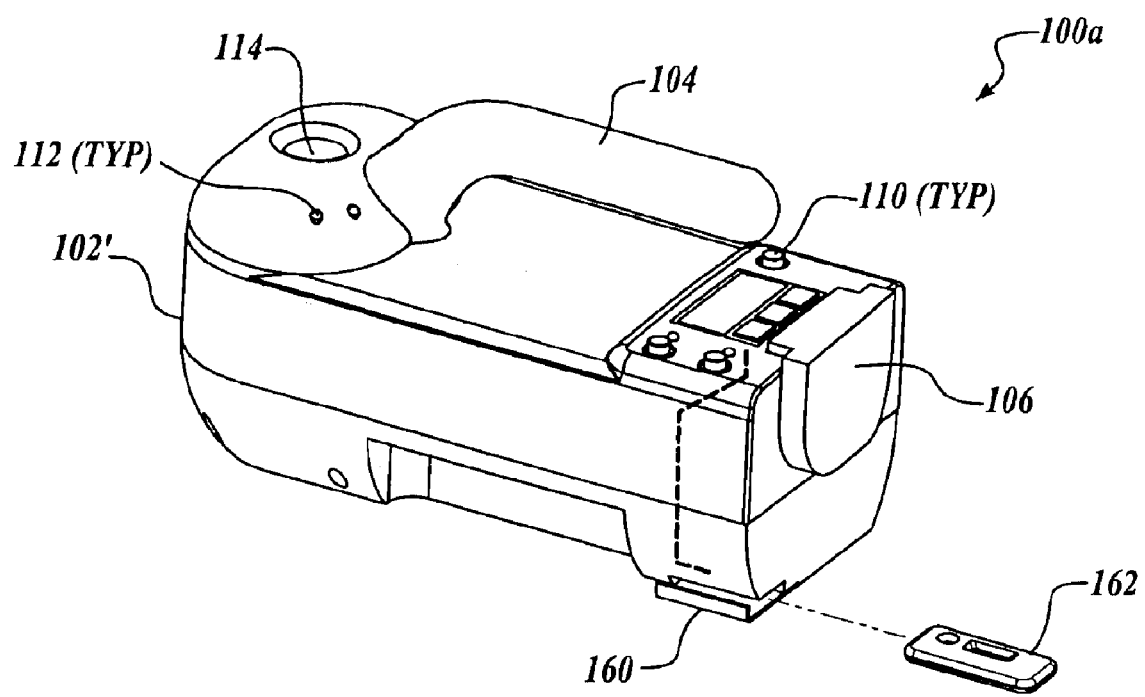
FIG. 9 is an isometric view of a portable sampler and integrated sensor unit in accord with yet another embodiment of the present invention, and showing a removable detection unit that, is used with the portable sampler.

FIG. 9 illustrates an air-monitoring unit 100a that has been modified to incorporate a real time detection unit 162. A housing 102' includes a slot 160. Preferably, housing 102' similarly includes an upper housing and a lower housing, as described above with respect to air-monitoring unit 100. As shown in FIG. 9, slot 160 is disposed in a lower housing portion of housing 102', although it should be understood that slot 160 could also be disposed in an upper housing portion of housing 102'. The purpose of slot 160 is to provide a recess into which detection unit 162 is inserted. Detection unit 162 might be designed to detect the presence of anthrax as evident from a color change appearing on a portion of the detection unit. After air-monitoring unit 100a has been operated for the desired time period, and a sample has been obtained in the sample reservoir of disposable fluid cartridge 120, a small amount of sample fluid is placed into detection unit 162. A specific color change on the detection unit indicates the presence of anthrax. An anthrax detection unit is readily available from Tetracore, Inc. Similar color change detection units for other agents are also available from the same company.

It should be noted that it is contemplated that other types of real time detection units can be integrated into portable air-monitoring unit 100*a*, and that the use of the anthrax detection unit described above is merely exemplary, and should not be considered limiting on the scope of the invention. For example, it is anticipated that the micro-fluidic, card-based detection units described above in conjunction with personal air-monitoring unit 10*a* could be incorporated into portable air-monitoring unit 100*a*. Of course, housing 102 would need to be modified to provide a slot for such a micro-fluidic card. Furthermore, in such an embodiment it would likely be preferable to change the path of the fluid line connecting combined impact collector and fan 134 to fluid port 118*c*, such that the sample fluid was directed instead to the micro-fluidic card. In such a case, either a portion of the sample fluid could be directed into the sample reservoir of disposable fluid cartridge 120 for archival purposes (or confirmation of results at a later time), or all of the sample fluid could be directed to the micro-fluidic card. Of course, as with personal air-monitoring unit 10*a*, other portable detection technologies readily adaptable to be employed as a disposable unit could be integrated into portable air-monitoring unit 100*a*.

It should be noted that portable air-monitoring units 100 and/or 100*a* can be adapted to operate according to several different sampling paradigms. As described above, the combined impact collector and fan is rotated for a defined period of time, and then rinsing is initiated once the combined impact collector and fan stops rotating. It is contemplated that portable air-monitoring units 100 and/or 100*a* can be automatically programmed to selectively operate for one of several different sampling cycle times, under the control of a programmable electronic controller that is included therein. Each different predefined sampling time cycle will be optimized for collecting a specific particulate.

In one contemplated embodiment, the rinse fluid reservoir and sample reservoir of the disposable fluid cartridge are combined, such that while the combined impact collector and fan is rotating, it is rinsed with the rinse fluid previously used. In such an embodiment, the rinse fluid is thus continually recycled and the concentration of the particulates in the rinse fluid will increase if the air drawn into the collector continues to include the particulates. It is further contemplated that a relatively large volume of rinse fluid can be provided (along with a correspondingly large sample reservoir), such that any time the combined impact collector and fan is rotating, fresh rinse fluid is used to rinse the combined impact collector and fan. Such a non re-circulated rinse is best for maintaining cell viability, which is critical if culturing techniques are employed in the detection method. A non re-circulated rinse is also preferable if a continuous sample feed is provided to the detector for ongoing, real time detection.

It is further anticipated that combined impact collector and fan 134 can be coated with a substance that increases the adhesion of particulates when in a first state (i.e., when in a dry state) and which enhances the removal of particulates in a second state (i.e., when in a wet state). One such type of coating undergoing empirical testing is a mixture of sugar and gelatin.

Preferred Geometrical and Elemental Aspects of a Rotating Arm Collector

As discussed above, a rotary impeller is a useful device for collecting and concentrating particulate matter from the air. As it spins, the impeller simultaneously performs two functions: actuating air flow in from an inlet and out through an outlet, and impacting particles entrained in the air onto itself. Although the concept of a rotary impeller is straightforward, there are many aspects of the design and use that affect its efficiency and performance. Furthermore, in terms of commercial viability of a product that includes a rotary impeller, there are many aspects of the design and use that affect the cost, reliability, reproducibility, manufacturability, and size. All of these factors contribute to the utility of the device.

Normally the rotary impeller is actuated by an electrically-operated motor (although conceivably other types of prime movers can be employed). This motor, which may be purchased from a supplier or custom built, is a major contributor to the cost and size of the complete impeller apparatus. The motor must be capable of rotating the impeller at the required speeds, which can be up to 30,000 rpm, although more preferable speeds are in the range of 8,000 to 15,000 rpm. It is preferable that the motor, while rotating the impeller at the desired speed, is operating within its intended range of performance in terms of utilizing an appropriate amount of voltage and current for the experienced load. The intended range is generally specified by the manufacturer, in the case of a purchased motor. If the motor is operating out of its intended range, there is an increased likelihood that the motor will fail after extended use of the impeller, whether that use is continuous or intermittent. The greater the actual operating conditions vary from the motor's intended performance range, the sooner that failure is likely to occur. It is preferable that the motor does not fail during the intended lifetime of the product. FIGS. 3A and 3B, described in detail above, illustrate an exemplary rotary impact collector and motor.

The load presented to the motor by the rotary impeller is determined by a plurality of factors. The most straightforward parameter is the rotation rate of the impeller. In general, any motor will require more power to operate at a faster speed, although some motor designs require only small additional increments of power to achieve faster rotation. The mass of the impeller is another major factor adding to the load on the motor. The impeller mass can be increased by numerous methods. One method is concerning the physical size; the overall mass will increase with increasing impeller diameter and by adding more or larger vanes. Another method that can increase the mass of the impeller is to change its material. Yet another method of increasing the mass of the load is to add material such as airborne particulate that becomes rigidly fixed to the impeller through impaction. In environments with large amounts of particulates, or when the rotary impeller is operated for long periods of time, substantial material can impact on the impeller, increasing its effective mass. Some environments may also contain very dense particles, such as microscopic iron filings, that can also have a dramatic effect on mass. The load on the motor is also affected by physical characteristics of the environment. The more viscous the air, the larger the drag forces will be on the impeller as it spins; thus the larger the load experienced by the motor. Air can become more viscous at lower temperatures, or at higher humidity. Finally, the load presented to the motor is also affected by the stability of the load itself. If the weight of the impeller is not distributed in an angularly symmetric fashion, or if the impeller wobbles during rotation, the load on the motor will be increased.

In terms of operation of the device incorporating a rotary impact collector (i.e. an impeller), it is preferable to minimize the load presented to the motor both to reduce the likelihood of failure by operating the motor outside of its intended range, and to reduce the overall power requirements of the motor. When considering a rotary impeller device that may be used remotely, it may be necessary to power the unit by battery or generator. In such cases, it is advantageous to minimize the amount of power required. This will reduce the size of battery required and the size of the generator required, and will increase the lifetime of the battery.

As discussed previously, there are a number of factors that affect the load presented to the motor. Because one of the intended functions of the rotary impeller is to collect particles, it is not feasible to reduce motor load by reducing the tendency of particles to impact on the impeller. It is also not feasible to limit the environments in which the apparatus is to be operated, as air samples need to be able to be operable under a wide variety of conditions. Therefore, the load on the motor is best limited by minimizing the mass of the impeller. While this can be achieved by limiting the diameter of the impeller and the number and size of vanes, the functionality of the impeller can be reduced by arbitrarily restricting these factors, without understanding how changes in the impeller to reduce mass will effect the functionality of the impeller. For example, making the impeller smaller, using fewer vanes, and using shorter vanes, each tend to decrease air flow rate and the amount of particles impacted. It is therefore necessary to balance the two parameters of motor load and collection performance to achieve the best possible compromise. It is noteworthy that it is possible to reduce the mass of the impeller (and therefore the load on the motor) without changing the geometry of the impeller by utilizing a less dense material. As will be discussed below, certain geometric aspects may allow fabrication techniques that enable less dense materials to be used (such as injection molding to be utilized), as compared with the densities of materials other traditional fabrication techniques require.

Two motor characteristics worthy of consideration are size and weight. In order for the rotary impeller apparatus to be portable, the overall size and weight of the system must be minimized. Both the size and the weight of the motor contribute significantly to the overall size and weight of the apparatus. Portable products fall into a number of different size classes. Some products can be considered portable if they can be placed on a motor vehicle. In other cases, it is necessary to be able to carry the object in a backpack. Still other cases require an object to be handheld. Finally, there are some cases where it is desirable to have an object so small and light that it can be affixed to a person (or that person's clothing/equipment), such as a device that fits in the breast pocket of a shirt or latches onto a belt. For devices that fall into the smaller categories, one advantage afforded by the miniature size is concealment for the purposes of hiding the apparatus. This may be advantageous if it is undesirable to cause alarm to persons in the vicinity of the apparatus, or if the user wishes to employ the apparatus in secrecy. For example, even the personal samplers disclosed in conjunction with FIGS. 1 and 5 (described above) are not sufficiently small to be readily concealed. The minimization of size and weight open new applications for a rotary impeller apparatus, and it is therefore advantageous to employ characteristics of the apparatus geometry that achieve these goals.

It is also desirable to minimize the noise produced by the motor. This is desirable for commercial applications of the rotary impeller product so as to minimize effects on personnel in the vicinity of the apparatus. For example, if a rotary impeller product were used in an office area to monitor the air, it would be preferable for the sound caused by the apparatus to be minimal. Low noise is also desirable for cases where a rotary impeller apparatus may be used in military operations. For example, if a soldier were wearing such an apparatus to monitor the air in his or her vicinity, it would be preferable for the apparatus to produce minimal noise so as to decrease the likelihood of revealing the presence of the soldier to enemy soldiers in the vicinity.

Finally, it is also preferable to minimize the cost of the motor. As in the case of many design criteria, the cost of the part must be balanced against the functional requirements of the part.

The motor can receive power from a number of possible sources. One is a battery that is integrated into the apparatus. Another source is a portable generator, such as those commonly employed by the armed forces during military operations. Another power source is standard alternating current available in any facility wired for electricity. In this case, the apparatus would incorporate a direct current power converter and a plug for accessing an electrical outlet.

In the case of a battery as a power source, it is preferable to minimize the size, weight, and cost of the battery while maximizing its lifetime. The battery lifetime can be considered as total apparatus operation time for a non-rechargeable battery, while it can be considered as operation time between charges and total number of possible charges for a rechargeable battery. The advantages of smaller size and weight of the battery are the same as for the motor discussed previously. It is preferable to have a battery with the longest possible lifetime, while also considering the cost of the battery. The lifetime of the battery is closely related to the power requirements of the motor, and is therefore related to the load presented to the motor.

There are numerous methods of fabrication for the rotary impeller and the impeller housing. Each fabrication method has certain limitations both in the geometry of the fabricated parts and in the materials used. The cost of each fabricated part is a major factor in deciding how the part will be used.

One fabrication method is traditional machining, where parts are fashioned from solid blocks of material by a combination of drilling, milling, and other processes well known to those familiar with the art of machining. In some cases, due to geometry, it is not possible to machine a part from a single block of material and it is necessary to form the part by adhering two parts that are machined separately. The adhesion of the two parts can occur by many techniques, including use of glue, epoxy, or other adhesive; use of heat or solvent welding; use of mechanical fasteners; or other means well known to those familiar with the art of adhering machined parts. In comparison to other fabrication methods, machining is often substantially more expensive, but has excellent precision and the turnaround time to receive a machined part based on a design can be very rapid.

Another fabrication method is a class comprised of various techniques for depositing material on a surface in a stepwise, layered fashion until a complete three-dimensional object is formed. Other technique belonging to this class is stereolithography. In comparison to other fabrication methods, this class of techniques is often the fastest way to generate a part from a design, but the precision of the part is usually poorer, while the cost is moderate.

Molding represents another method of fabrication. In this case, molds must be created that can be used as a basis for forming individual parts. When injection molding is used, the parts will often be made from plastic which is injected as a liquid into the closed mold. When the plastic cools and solidifies, the parts can be removed. In all modes of molding, some additional machining of parts may be required after the molding process to perfect features not attainable by molding alone. When molds are created, they are generally rated for a certain number of parts until the mold itself fails. More expensive molds are usually capable of creating more molded parts. For example, a mold that costs $10,000 may be able to create an average of 10,000 parts before failure, while a mold that costs $50,000 may be able to create an average of 100,000 parts before failure. Molding has a higher overhead cost associated with it than many other fabrication methods because of the up-front cost of the mold. However, in the case of a mold that is able to generate many parts, after all costs are considered, the parts can be very inexpensive. The time to produce parts is very short once the mold has been created. The precision of the technique depends on the material used in the mold and type of part being created. In some cases, the precision is excellent. In other cases, it is necessary to allow for substantial tolerance in the apparatus design due to expansion and contraction variations in the molded parts.

The fabrication method has impact on the performance and usage of the assembled apparatus. One major consideration is the overall cost of the parts and how this affects the pricing of the apparatus. The price of the parts also affects consideration of cleaning or non-cleaning of the unit. For example, a rotary impeller apparatus is designed to collect biological particulate from the air. Therefore, all surfaces exposed to the air may become contaminated with biological matter. This poses two problems. One is that it may become impossible to determine the location of origin of biological matter if the apparatus is used in numerous locations due to contamination among the multiple uses of the apparatus. The other problem is that because the apparatus concentrates biological matter, it may produce a health risk to the user by concentrating dangerous airborne bacteria in the vicinity of the user. These problems can be avoided by either decontaminating the parts in between uses or by discarding the parts exposed to concentrated particulate after each use. If the cost of each rotary impeller and impeller housing is considerable, it is not feasible to discard the parts after each use. However, if the parts are produced by injection molding, the cost of each part should be low enough to make the parts disposable. This usage model is preferable over decontamination because the cost is roughly equivalent, since decontamination requires additional reagents and because decontamination is not entirely effective, whereas replacing the contaminated parts will eliminate the source of contamination.

A set of characteristics can be defined for controlling the overall performance of the rotary impeller. One that has been previously mentioned is the power requirement, which refers not only to the operating voltage and current, but also to the duration over which it must be supplied.

Another performance characteristic is air flow rate through the apparatus. In general, it is preferable to have as high an air flow rate as possible, without compromising the ability of the apparatus to collect particulates, without causing severe damage to the collected particulate, and without dramatically increasing the power requirement.

Perhaps the most important characteristic is the collection efficiency of the impeller. This is a measure of the fraction of particulates contained in the air that passes through the impeller that is actually collected by the impeller. For example, during one interval of sampling, a rotary impeller apparatus may draw 1000 liters of air over a period of several minutes. If the air contains an average of 100 bacteria per liter of air, then approximately 100,000 bacteria will pass through the apparatus during that interval. If 70,000 bacteria are recovered from the apparatus, then the collection efficiency is 70%. Note that the collection efficiency is likely to vary depending on the size, deformability, and surface characteristics of the particulate. The collection efficiency is comprised of two main efficiency values: the impaction efficiency, which is a measure of the fraction of particles that impact and adhere to the impeller, and the recovery efficiency, which is a measure of the fraction of impacted particles that are successfully rinsed from the surface and covered in the liquid sample.

A number of factors may reduce the collection efficiency. For example, it is possible for some of the rinse fluid, which contains successfully impacted and recovered particles, to remain inside the impeller housing due to drainage failure. In this case, the particles are never added to the final sample and therefore do not contribute to the count of successfully collected and recovered materials.

Surface roughness of the impeller plays a major role in impaction efficiency. All of the manufacturing methods discussed previously include the ability to introduce various amounts of surface roughness. In the case of particle impaction, increased surface roughness aids in particle retention during the impaction process. This is likely due to increased friction forces between the surface and the particle, which tend to counteract shear stress forces that would prevent adhesion between the particle and the surface. The increased surface roughness may also provide increased purchase points for the particle to become seated on the surface of the impeller. In the interest of maximizing impaction efficiency, it is therefore preferable to use increased surface roughness.

Surface roughness also plays a major role in recovery efficiency. Unfortunately, it has the opposite effect as it has on impaction efficiency. Specifically, increased surface roughness inhibits particle recovery during the rinsing process. The mechanisms are likely to be identical to the basis for increasing impaction efficiency. Specifically, the increased surface roughness creates more friction between the particles and the surface, meaning that larger shear stress forces are required to separate the particles. Also, the additional surface roughness likely creates purchase points for the particles, which are substantially more difficult to rinse than a flat surface.

It is noteworthy that while it may be desirable to increase the surface roughness of the impeller, it is usually undesirable to increase the surface roughness of the impeller housing.

The extent of inhibition of particle recovery efficiency by surface roughness depends on the type of rinsing performed. As described above, rinsing may be effected by several methods. A first method is a continuous liquid rinse during the sampling interval, when the impeller is rotating. A second method is a liquid rinse occurring after an interval of sampling in the absence of liquid. This method would also be executed while the impeller is rotating. A third method involves removal of the impeller from the impeller housing and rinsing using an external rinse station. The detrimental effect of surface roughness on recovery efficiency refers specifically to the first two methods of rinsing. In the case where the impeller is removed from the housing, the extent of the effect of surface roughness depends on the type of external rinsing used.

External rinsing of a removed impeller can be achieved by various techniques (see the related discussion above with respect to FIGS. 4A and 4B). One class of external rinsing methods includes placing the impeller in a volume of liquid inside a container such as a beaker, box, or bag. Then, the container can be manually agitated, or subjected to mechanical agitation from an apparatus such as a sonicator or shaker.

In the case of external rinsing involving sonication, surface roughness of the impeller has very little effect on recovery efficiency. This is believed to be because sonication is a very vigorous method of agitation which produces forces on particles that are significantly different from the shearing forces of a flowing liquid. In the case where sonication is to be used, a preferred embodiment of the apparatus is to use an impeller with considerable surface roughness.

In contrast, in the case of external rinsing achieved using manual agitation or use of a shaker (i.e. subsonic agitation), the surface roughness has a more substantial effect on recovery efficiency, and a preferred embodiment employs only a moderate amount of impeller surface roughness.

Figure 10:
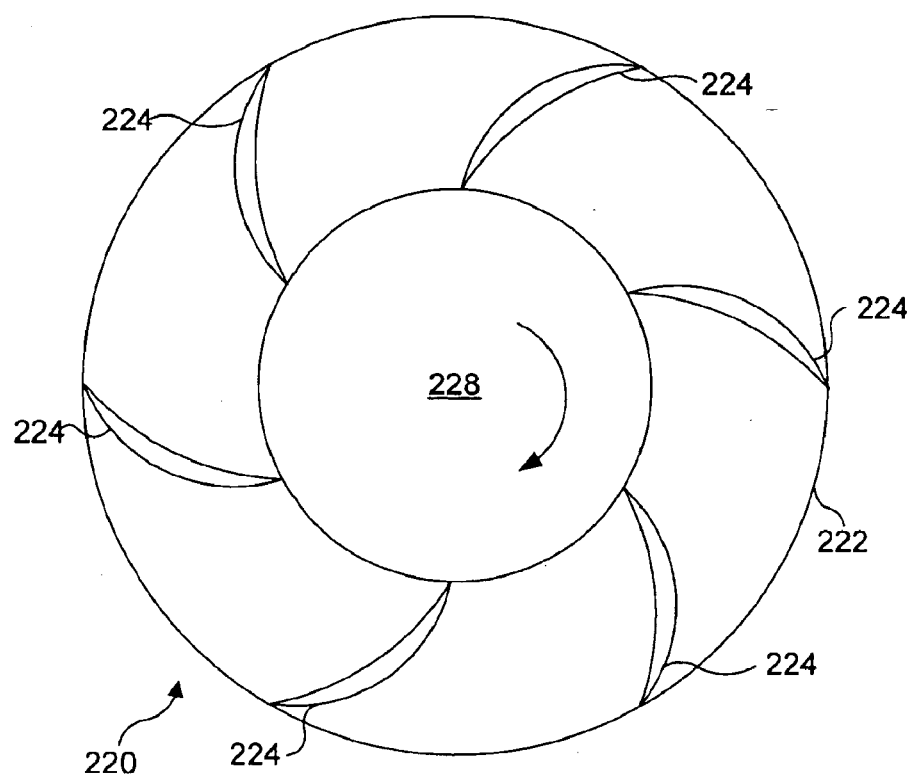
FIG. 10 is a plan view of a combined impact collector and fan used in both embodiments of the present invention.
Figure 11:
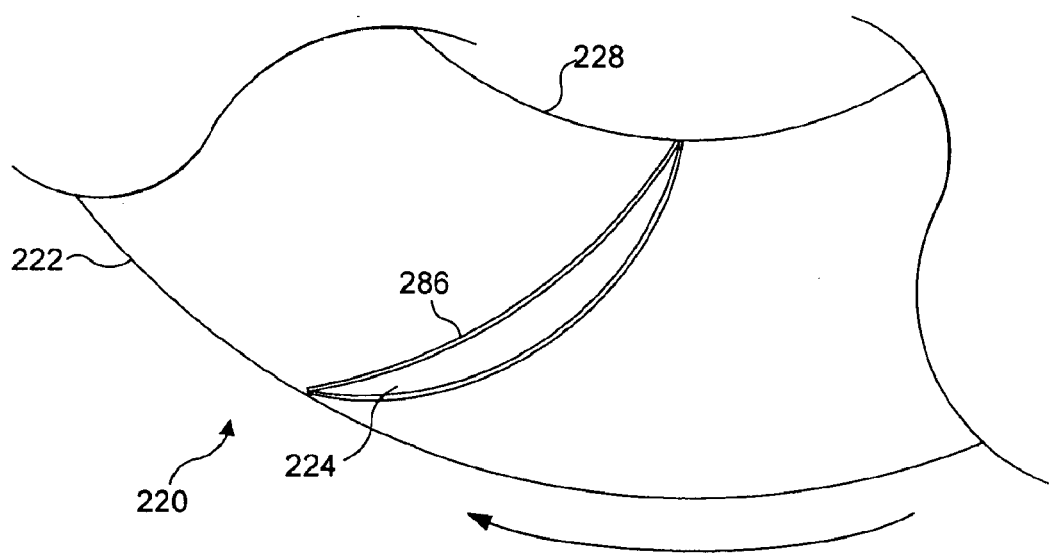
FIG. 11 is a plan view of a portion of the combined impact collector and fan shown in FIG. 10, enlarged sufficiently to illustrate an impeller vane.

FIG. 10 is a plan view an impeller with a plurality of vanes and FIG. 11 is an enlarged view of a vane. A combined impact collector and fan 220 is rotatably mounted within a cavity, such as the housings shown in FIGS. 1, 2, 3 and 4A, and discussed in detail above. Combined impact collector and fan 220 includes a round plate 222 on which are formed a plurality of impeller vanes 224, spaced apart around the top surface of plate 222 and disposed at an angle so as to serve both as a centrifugal fan that moves air into such a housing from an external ambient environment and as an impactor on which particulates are separated from the air drawn into the cavity. Plate 222 includes an opening 228. Impeller vanes 224 are thus curved, so that when plate 222 is rotated, the impeller vanes draw air through an opening in such a housing, moving the air in which particulates are entrained from the ambient environment into the housing and collecting the particulates. Specifically, in addition to drawing air (or other gaseous fluid) into the housing, impeller vanes 224 also impact against particulates, thus separating the particulates from the air drawn into the cavity by at least temporarily retaining the particulates on the surfaces of the impeller vanes on which the particulates have impacted. Furthermore, particulates are also collected on the surface of plate 222.

Experimental results have demonstrated that the majority of impacted particulates are located on the faces of the vanes on the impeller. Specifically, the particles adhere to the side 286 of the vanes that face the direction of rotation of the impeller (note the arrows indicating the direction of rotation in FIGS. 10 and 11). This is unsurprising since the motion of the impeller is the likely cause of the impaction even between the vanes and the particles. It has been experimentally demonstrated that increasing the height of the vanes increases the impaction efficiency, most likely because more of the air is directed against the vertical surface of the vanes and it is substantially more unlikely that particles can "hurdle" the vanes. In practice, the vane height can be increased or decreased within certain practical limits. If the vane height is decreased to zero, this is equivalent of having no vanes on the surface of the impeller. If the vane height is increased to be on the same order of magnitude as the diameter of the impeller, this will be a very awkward structure to rotate in a balanced fashion. This structure is also very difficult to rinse efficiently. Furthermore, the structure would require much more power to actuate, eliminating the advantage of the low-power requirement. In practice, the optimal balance of impaction efficiency, ability to effectively rinse, and ability to effectively rotate at a high rate, is reached when the ratio of vane height to impeller diameter is in the range of 0.01 to 0.2. This ratio assumes measurement of the average vane height, as the height may not be constant along the entire length of the vane.

The height of the vanes also impacts the air flow rate produced by the apparatus. Experimental results demonstrate that while even a flat disc (with no vanes) will produce some outward air flow, it is the vanes themselves that produce the majority of the air flow. Having taller vanes will produce a larger air flow rate for the same rotation rate, at the expense of requiring more power.

The number of vanes used will also affect air flow rate, collection efficiency, and the power requirement. More vanes will increase air flow rate and will also increase collection efficiency by decreasing the amount of time available to particles to escape between the vanes. It is preferable that the vanes be evenly spaced around the impeller so as to present a balanced load to the motor. An unbalanced load or a load that is balanced but unevenly spaced will tend to cause much more wear on the motor than a balanced, evenly spaced load.

One of the factors that aids in particle impaction is penetration of the particles entering the apparatus to a depth below the height of the top edge of the vanes. Since some of the air does not reach this depth but rather turns and flows over the vanes, particles entrained in this air will penetrate below this level only through their own inertia; specifically, their downward momentum will cause the particles to move from their original air stream into a region further below. The extent to which the particles penetrate to a lower depth is dependent on their stopping distance, which is an aerodynamic property of particles that depends in part on the particle's diameter. Larger particles will have a longer stopping distance, meaning that they will move further due to momentum effects. All particles that are located below the top edge of the vanes have a much higher likelihood of being impacted by the vanes.

Referring once again to FIGS. 10 and 11, impeller vanes 224 are situated on the top surface of round plate 222. Impeller vanes 224 can begin at the center of round plate 222 or alternatively can begin further radially outward from the center of round plate 222. Impeller vanes 224 can end at the outer edge of round plate 222, or alternatively can end further radially inward from the outer edge of the round plate.

FIGS. 12 and 13 show combined impact collector and fan 220 mounted into an exemplary particle impactor 210. Note FIG. 12 is an exploded view and FIG. 13 is a side elevational cross sectional view. Particle impactor 210 includes a cylindrical shaped housing 212 formed from a metal, or alternatively molded or otherwise formed from a relatively lightweight polymer material. Housing 212 defines an internal cylindrical cavity 214. Cavity 214 is covered with a plate 216 that is held in place by a plurality of threaded fasteners 218, which pass through orifices 219 in plate 216 and are then threaded into blind threaded openings 221. Openings 221 are spaced apart around the top surface of the underlying cylindrical portion of housing 212. An O-ring 223 is seated in this top surface adjacent to blind threaded openings 221 and provides a seal against the under surface of plate 216.

Combined impact collector and fan 220 is rotatably mounted within cavity 214. Combined impact collector and fan 220 includes round plate 222 on which are formed the plurality of impeller vanes 224, spaced apart around the top surface of plate 222 and disposed at an angle so as to serve both as a centrifugal fan that moves air into cavity 214 from an external ambient environment surrounding impact collector 210, and as an impactor on which particulates are separated from the air drawn into the cavity. Impeller vanes 224 are thus curved, so that when plate 222 is rotated, the impeller vanes draw air through an opening 228 formed in an annular plate 226 that is affixed over the top of impeller vanes 224, moving the air in which particulates are entrained from the ambient environment into cavity 214 and collecting the particulates. Specifically, in addition to drawing air (or other gaseous fluid) into cavity 214, impeller vanes 224 also impact against particulates, thus separating the particulates from the air drawn into the cavity by at least temporarily retaining the particulates on the surfaces of the impeller vanes on which the particulates have impacted. Furthermore, particulates are also collected on other surfaces within the cavity on which the particulates impact, including for example, the surfaces of plate 222, annular plate 226, and an inner surface 274 of cavity 214. Clearly, the greater the mass of the particulates, the more likely it will be that they will be separated from air or another gaseous fluid by the impact collector.

It should be pointed out that no additional fan or device is required to cause air or other fluid in which particulates are entrained to move into cavity 214. In virtually every other type of impact collector incorporating a rotating arm intended to separate particulates from a gaseous fluid as a result of the impact of the particulates against the rotating surface, a separate fan assembly is required to move the gaseous fluid into the vicinity of the rotating arm assembly. In contrast to such prior art devices, the present invention includes combined impact collector and fan 220, which both draws air or other gaseous fluid into the cavity and impacts the particulates to separate them from the air or other gaseous fluid in which they are entrained.

While other types of materials can be used, combined impact collector and fan 220 is preferably fabricated from a plastic material or other types of lightweight, low angular momentum or low inertia materials to facilitate its rotation. Annular plate 226 is preferably adhesively attached to the tops of impeller vanes 224. Plate 222 is attached to a drive shaft 272 with a threaded fastener 273 (see FIG. 13) that extends down through the center of plate 222 into the end of the drive shaft. A mounting plate 230 rests on the top of a plurality of standoffs 232 and includes an annular skirt 230a (see FIG. 13) that depends downwardly from the perimeter of the mounting plate. Drive shaft 272 is coupled to a motor 270. If desired, a threaded drain port 236 can be provided in a bottom 234 of cavity 214 to facilitate rinsing of the combined impact collector and fan 220.

A threaded drain port 236 is provided in a bottom 234 of cavity 214 and is disposed adjacent a periphery of the cavity. During usage of particle impactor 210, a receiver 238 is threaded into threaded drain port 36 and is provided with mating threads 240 around its inlet to facilitate its rapid attachment and removal from housing 212. It is alternatively contemplated that the receiver may be held in place with a quick-release fastener (not shown) or by any other suitable mechanism, including a friction fit using an elastomeric fitting that is disposed around the neck of the receiver. Receiver 238 serves as a reservoir and includes a side arm 242 through which part of the air or other gaseous fluid that flows from cavity 214 is exhausted after the particulates entrained therein have been separated by impact with impeller vanes 224 or other surfaces within the cavity. As will be evident from the dash lines shown extending past each side of a motor 270, most of the air or other gaseous fluid flows between annular skirt 230a and a hub 235 (see FIG. 13) formed in the center of the bottom of the cavity, and then exits the cavity around motor 270, thereby providing cooling for the motor.

An outlet port 244 is included in receiver 238, adjacent its bottom, and is connected through a flexible tube 246 to an inlet 248 of a centrifugal pump 250. A peristaltic (or other type) pump may be employed instead of the centrifugal pump shown in FIG. 12. It has been contemplated (but not shown in the drawing figures) that a Venturi pump might be fitted into an opening 260 so that the velocity of the air or other gaseous fluid drawn into cavity 214 would create a sufficiently low pressure in a Venturi tube to draw liquid from reservoir 238. This liquid would be injected into the air or gaseous fluid entering the cavity, using much the same method that is used for mixing gasoline with the air entering a cylinder in automotive carburetors. Use of such a Venturi device would enable centrifugal pump 250 to be eliminated, but would also eliminate a three-way valve 253, since the flow of liquid from the reservoir induced by a Venturi effect cannot readily be redirected through a three-way valve.

Figure 12:
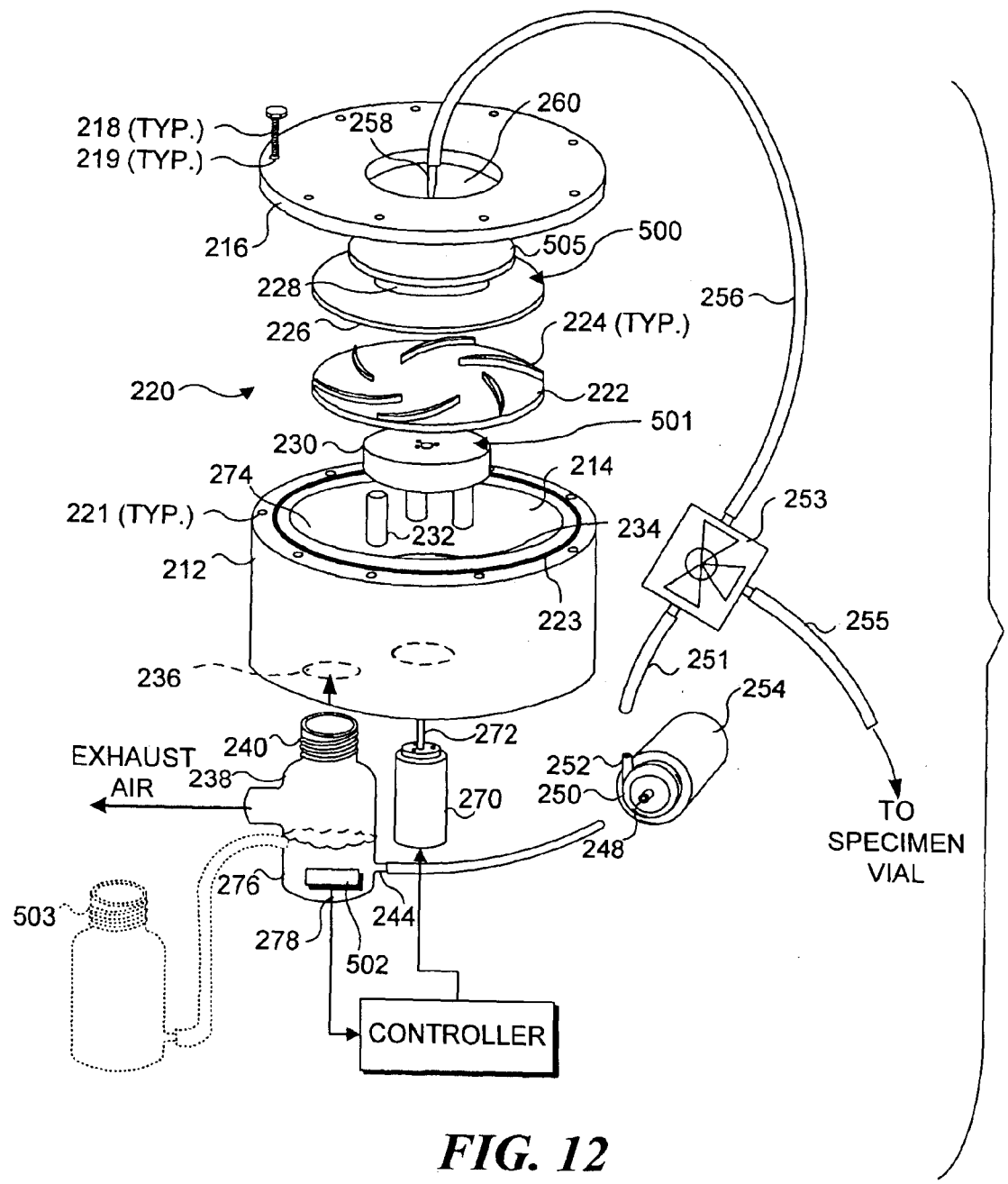
FIG. 12 is an exploded isometric view of a particle impactor including efficiency enhancing elements in accord with the present invention.

In the embodiment shown in FIG. 12, centrifugal (or other type) pump 250 is driven by a separate motor 254. The centrifugal pump includes an outlet 252 that is connected to a flexible conduit 251. The other end of flexible conduit 251 is connected to three-way valve 253 which is controlled with an electrical signal. A flexible conduit 256 connects one outlet port of three-way valve 253 to a nozzle 258, which is disposed above inlet port 260 in cover plate 216. Liquid flowing from nozzle 258 is directed through inlet port 260 toward opening 228 in the combined impact collector and fan that is mounted within cavity 214. Nozzle 258 creates a stream of a liquid 276 that is contained within the reservoir provided by receiver 238. The liquid forms droplets that are carried by air drawn into opening 228 and these droplets wash over the surfaces of impeller vanes 224 and other surfaces within cavity 214, carrying the particulates that have been temporarily retained thereon away. The particulates are carried by the liquid down inner surface 274 toward bottom 234 of cavity 214.

Another outlet port of three-way valve 253 is connected to a flexible conduit 255, which is directed toward a specimen vial or other specimen collection container (not shown). The three-way valve can be selectively actuated by an operator to direct liquid flowing from centrifugal pump 250 into either flexible conduit 256 for circulation back into cavity 214, or into flexible conduit 255 for withdrawal of a specimen of the particulates being collected. Further options for recovering a specimen of the particulates collected are discussed below.

In addition to clearing particulates from the surfaces on which they have impacted, the liquid directed into cavity 214 through nozzle 258 also serves to entrain sub-micron particulates carried by the air or gaseous fluid that is drawn into the cavity in droplets. The entraining droplets have substantially greater mass than the sub-micron particulates alone and are thus more readily separated from the air or other gaseous fluid by impact against surfaces within cavity 214. These sub-micron particulates are thereafter carried into receiver 238, as described above.

The liquid carrying the particulates that were previously separated from the air or other gaseous fluid drawn into cavity 214, flows through threaded drain port 236 in bottom 234 of the cavity and into receiver 238. Over time, if the particulates separated from the air are solid or semi-solids and if they are denser than the liquid in the reservoir, a residue 278 of the particulates that have been collected will accumulate in the bottom of receiver 238 as the particulates settle out of the liquid. This residue can be readily removed for analysis or other tests. In other instances, where the particulates entering inlet port 260 are liquid aerosol that is miscible in liquid 276 (i.e., the liquid injected to wash the particulates from the impeller vanes), or is less dense than that liquid in the reservoir, the particulates washed from the impeller vanes will continue to increase in concentration within liquid 276, forming a readily collected specimen of the particulates within the reservoir. When this specimen is analyzed, the chemical composition of the aerosols or materials comprising the particulates can be readily determined. It is also noted that the particulates drawn into the impact collector may comprise bacteria or spores, which are also readily analyzed. A sample of liquid 276, with the particulates contained therein comprising a specimen are readily withdrawn from receiver 38 by actuating three-way valve 253 so that it pumps the specimen from the receiver and empties flexible conduit 246 into a specimen vial through flexible conduit 255.

Once the receiver has been emptied, a sterilant, or disinfecting solution such as hydrogen peroxide solution, may be circulated through the impact collector from receiver 238, using centrifugal pump 250. Use of the sterilizing solution would then be followed by several rinses to prepare the impact collector to receive another specimen.

It is contemplated that a small heating element (not shown) may be provided either around, adjacent to, or inside the receiver to ensure that liquid 276 does not freeze. Provision of such a heating element should be necessary only if the device is exposed to an ambient temperature that is below the freezing point of the liquid in the receiver.

To rotate the combined impact collector and fan 220, motor 270 is provided. The motor is connected to mounting plate 230 using a plurality of threaded fasteners 275 (only one of which shown in FIG. 13). As noted above, drive shaft 272 of motor 270 is connected to plate 222 using threaded fastener 273. Although not shown, drive shaft 272 may also include a spline, or a flat surface against which a set screw can be tightened to ensure that the combined impact collector and fan is rotatably driven by drive shaft 272 when motor 270 is energized.

A power supply and pump/valve control 262 provides electrical current for energizing pump motor 254 and motor 270 via a power lead 268. The position of three-way valve 253 is controlled by the operator using power supply and pump/valve control 262 via a control line 257. The electrical current supplied to pump motor 254 is conveyed through a power lead 266. Optionally, a speed control 264 is included to enable an operator to selectively control the speed of motor 270. In a preferred embodiment, motor 270 is a Micromole Inc. brushless DC motor, Series 1628, although other similar types of motors are equally usable for this purpose. Optional speed control 264 can be used to adjust the rotational speed of motor 270, and thus to enable the rotational speed of the combined impact collector and fan to be set within the range of about 80 to 50,000 rpm (or greater if a motor capable of higher speed is used). The specified speed range corresponds to a rate of fluid flow through the impact collector of 80 liters per minute to 540 liters per minute. Substantially higher flow rates may be required for specific applications of the flow impactor. Generally, it is preferable to operate the impact collector at a higher rotational speed since it has been determined that the efficacy of particulate collection improves with increased rotational speed of the combined impact collector and fan. While optional speed control 264 may provide for continuously variable speed within the range of motor 270, it is more likely that a multi-position switch would be provided to select the desired speed, for example, from a low, medium, or high speed option. Note that control line 257, power supply and pump/valve control 262, optional speed control 264, power lead 266, and power lead 268 are only shown in FIG. 13.

As described above, air enters the apparatus through inlet port 260, which is defined as a hole in cover plate 216. The air orifice may be further defined by opening 228 in annular plate 226, which may or may not be present on top of impeller vanes 224. As described above, it is beneficial for particulate entering with the air to be directed perpendicularly toward round plate 222 so that the material will penetrate to a depth below the top of impeller vanes 224. However, if impeller vanes 224 begin near the center of round plate 222, air in the center of the round plate, opening 228, and inlet port 260 will tend to form a vortex, meaning that it will attain a substantial angular velocity in the same direction as the rotation of round plate 222. This angular velocity will be imparted to the particulate matter, changing the momentum of the matter, making it less likely that the material will penetrate toward round plate 222 below the top of the angular vanes. For this reason, it is preferable to begin impeller vanes 224 at a radial distance measured from the center of round plate 222 that is further from the center of the round plate than the circumference of each of opening 228 and inlet port 260.

FIG. 15 clarifies this issue. Note that impeller vane 224*b* extends into a portion of plate 222 that corresponds to opening 260 (note the dashed lines extending from opening 260 to plate 222). Impeller vane 224*b* has a less than optimal configuration, as the portion of impeller vane 224*b* extending toward the center of plate 222, beyond the dashed line, will likely induce a vortex. In contrast, impeller vane 224*c* does not extend into that portion of plate 222 that is immediately adjacent to opening 260, and thus impeller vane 224*c* is less likely to induce a vortex. Note the additional elements shown in FIGS. 12 and 13 (pumps, fluid lines, etc., have been omitted to achieve a simple drawing emphasizing the configuration of the impeller vanes).

The likelihood that a particle impacts the surface of any of impeller vanes 224 depends on the angular velocity of round plate 222, which defines the amount of time required for impeller vanes 224 to pass through the air proximal to the top face of round plate 222. This time requirement can be further reduced by adding more impeller vanes 224, as this would reduce the distance that each of the impeller vanes needs to travel to pass through all of the air. The upper limit of the number of impeller vanes 224 that can be used is determined by the practical limit of the number that can fit. Each of impeller vanes 224 must have a finite thickness associated with providing dimensional stability and mechanical strength. Due to crowding near the center of round plate 222, a limited number of impeller vanes 224 can actually be employed. For example, if the vanes begin at a distance measured radially of 1 cm from the center of round plate 222 (regardless of the diameter of the plate), this provides a circumference of approximately 31.4 mm. If each of impeller vanes 224 has a thickness of 1 mm, it will be possible to assemble up to 31 impeller vanes 224 in a rotary impact collector. Adding additional impeller vanes 224 has the drawback of increasing the mass of the impeller, and therefore the load presented to motor 270.

Figure 14:
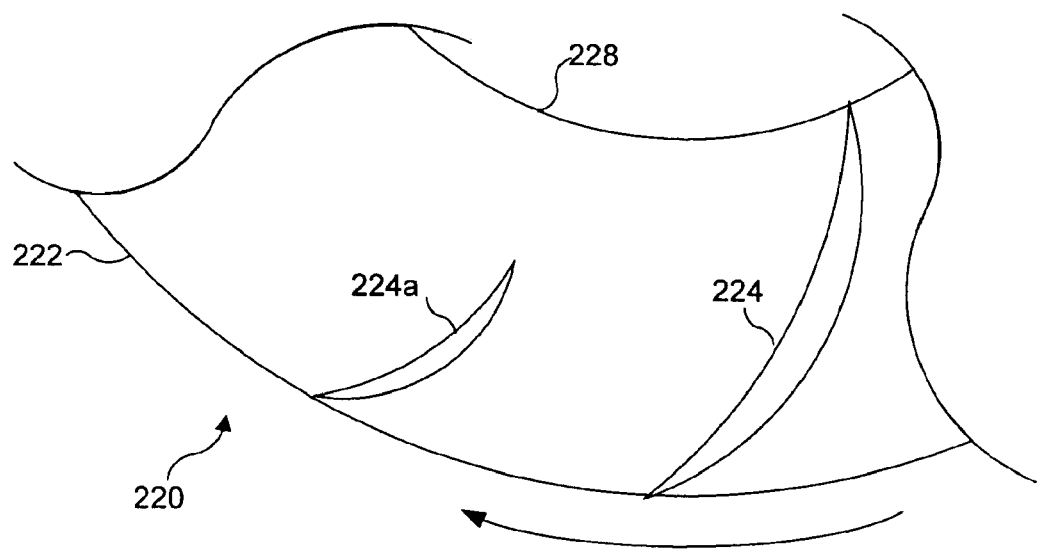
FIG. 14 is a another plan view of a portion of the combined impact collector and fan shown in FIG. 10, enlarged sufficiently to illustrate a modified impeller vane.

Furthermore, adding additional impeller vanes 224 increases the tendency to create a vortex in the air in the center of round plate 222, opening 228, and inlet port 260. As discussed above, the angular velocity induced by this vortex reduces impaction efficiency of the rotary impeller apparatus. This problem can be ameliorated by changing a number of the impeller vanes 224 to a truncated impeller vane 224*a* shown in FIG. 14, each of which are a fraction of the length of impeller vanes 224. Each truncated impeller vane 224*a* begins at a distance further outward from the center of round plate 222 than do impeller vanes 224, and end at the same distance from the center of round plate 222 as impeller vanes 224. Truncated impeller vanes 224*a* have been shown experimentally to have negligible effect on motor load or air flow rate while providing an increase in particle impaction efficiency. Truncated impeller vanes 224*a* can range in length from 0.1 of the length of impeller vanes 224 up to 0.9 the length of impeller vanes 224. Any ratio of truncated impeller vanes 224*a* can be used in proportion to the number of impeller vanes 224 employed.

Use of annular plate 226 is optional in the design of the rotary impeller. When used, it is affixed to the top edges of impeller vanes 224. When present, it substantially increases impaction efficiency of the apparatus by eliminating the tendency of particles to travel over the top of impeller vanes 224. Addition of the annular plate 226, however, substantially increases the mass of the complete impeller, which includes round plate 222, impeller vanes 224, and plate 226 (when present). This increases the load presented to drive shaft 272 of motor 270. Therefore, unless it is acceptable to use a larger motor, it is preferable to use round plate 222 with impeller vanes 224 (i.e. a combined fan and impact collector) without annular plate 226. When a larger motor (or a slower rotational rate) is acceptable, then it is preferable to utilize annular plate 226.

Referring again to FIG. 12, based on the lengths of various elements, a gap 500 (see FIG. 12) will be present between the top face of annular plate 226 and the bottom face of cover plate 216. Alternatively, if annular plate 226 is not used, gap 500 is produced between the plane defined by the top edges of impeller vanes 224 and the bottom face of cover plate 216. The size of gap 500 is determined by the lengths of other parts, including the height of housing 212, the thickness of mounting plate 230, and the length of standoffs 232. Is has been experimentally demonstrated that the size of gap 500 does not substantially affect the operation of the rotary impeller with a range in gap height between approximately 0.2 mm to approximately 2.5 mm. However, a difficulty may arise when it is desired to fabricate the apparatus by injection molding. There is a degree of uncertainty in the final dimensions of any part fabricated by injection molding, such that any part is assigned a tolerance value associated with the dimensional uncertainty. When numerous parts fabricated by injection molding are combined together, as is the case with the rotary impeller, a total tolerance along one dimensional axis can be defined that is the sum of the tolerances of the individual parts along that dimensional axis. In the case of the rotary impeller, based on knowledge in the art of injection molding, a total tolerance along the axis parallel to drive shaft 272 is between 0 mm and 2 mm. Therefore, if gap 500 is designed to be less than 2 mm, it is possible that the assembled apparatus will not function because the actual gap produced upon assembly is 0 mm (due to variations in the injection molding process). Such an apparatus will not function properly because of the friction between the bottom face of cover plate 216 and the top of annular plate 226 (or, when no annular plate 226 is used, the top edges of impeller vanes 224). Therefore, it is necessary to design the height of gap 500 to be at least 2 mm, preferably at least 2.2 mm, to ensure that the apparatus functions properly upon assembly if the parts are fabricated by injection molding. In the event that a more precise fabrication method is used, or if the tolerance of the injection molding process is improved, then it is possible to design the height of gap 500 to be less than 2 mm.

A similar situation exists with bottom gap 501 (see FIG. 12), a dimension defined by the space between the bottom face of round plate 222 and the top face of mounting plate 230. If bottom gap 501 measures 0 mm upon assembly, the device will not function properly due to friction between the two opposed faces, preventing the round plate from turning freely. Thus bottom gap 501 should be designed to be at least 2 mm, to ensure that the apparatus functions properly upon assembly if the parts are fabricated by injection molding.

Other design features will increase the quality of parts formed by injection molding. For example, impeller vanes 224 should be designed with "draft", which is laterally extending material at the base of each feature to accommodate removal from the injection mold. Also, it is preferable if impeller vanes 224 do not extend all the way to the outer edge of round plate 222 but rather stop at least about 1 mm before the outer edge. FIG. 15 shows an impeller vane 224d whose base includes a draft 510. Note that an upper portion 512 of impeller vane 224d does not extend laterally to the extent that draft 510 does.

A surface within cavity 214 forms bottom 234. It is preferable to introduce a slope in bottom 234 of cavity 214 such that fluid preferentially drains by force of gravity down to a receiver 238. FIG. 16 illustrates a housing modified to include a slope 212d in the lower portion of the housing to facilitate the collection of rinse fluid in receiver 238.

When liquid 276 is introduced into cavity 214 to rinse the surfaces of round plate 222 and impeller vanes 224, the recovery efficiency of the apparatus is adversely affected by liquid 276 that becomes permanently resident inside cavity 214 (i.e. liquid that does not ever return to receiver 238). Even if particles are successfully recovered from rinsed surfaces and entrained into liquid 276, these particles are regarded as having never been collected since the portion of liquid 276 containing them is inaccessible. A common location where portions of liquid 276 become permanently resident is in the annular region located at the intersection of housing 212 and cover plate 216. In this region air velocity is slow, and liquid that enters this region tends to adhere to the walls and cease motion. This region can be eliminated by providing an inwardly-curving or inwardly-angled inner surface of housing 212 proximal to where housing 212 adjoins to cover plate 216. Similarly, other regions inside the cavity that would benefit from providing an inwardly-curving or inwardly-angled surface occur where bottom 234 of cavity 214 meets the surface of the hub 235 and where bottom 234 of cavity 214 meets the inner surface of housing 212. Again, FIG. 16 illustrates a housing modified so that curved surfaces 212e (disposed generally at the intersection of the upper portion of the housing and the sides of the housing) and 212f (disposed generally at the intersection of the bottom portion of the housing and the sides of the housing) to reduce the likelihood that rinse fluid will become trapped in the housing.

As described above, nozzle 258 introduces liquid 276 through cover plate 216. In practice, it is preferable to locate nozzle 258 above the location of the inside edge of impeller vanes 224, rather than any location closer to the center of cover plate 216. In this manner, liquid 276 contacts the regions where particles are likely to impact round plate 222 and impeller vanes 224, rather than additionally rinsing the region of round plate 222 proximal to the center of the round plate. The injection of liquid 276 can be achieved by a continuous fluid stream or by drop wise addition. The selection of injection method depends on how much final sample volume can be tolerated and the desired recovery efficiency. The more liquid 276 that is used, the more efficient the rinse will be, but the larger and less concentrated the final sample will be. FIG. 15 shows a nozzle 258a proximate impeller vane 224c, as opposed to be disposed proximate a center of plate 222. Note the fluid line feeding nozzle 258a (see FIGS. 12 and 13) has been omitted for simplicity.

It is beneficial to add a sensor 502 (see FIG. 12) to monitor the level of liquid 276 in receiver 238. During the rinsing process, liquid 276 evaporates due to friction and heat inside cavity 214. Consequently, the total amount of liquid 276 present in the apparatus decreases over time, which can adversely affect recovery efficiency. In such cases, it is useful to employ a make-up reservoir 503 (see FIG. 12) that contains additional liquid not initially included in the rinse cycle. When sensor 502 determines that the level of liquid 276 has fallen below a certain value, additional fluid can be introduced from make-up reservoir 503 to keep the volume of liquid 276 present in the apparatus roughly constant. Sensor 502 can be simply implemented using a pulsed light source and photo receiver, such as a photodiode, that spans across the receiver 238 at a particular level (not separately shown). The amount of light transmitted across the receiver depends on whether or not the liquid level exceeds the location of the light path, thereby allowing determination of whether the receiver 238 is filled to the particular level. Many other embodiments of sensor 502 are possible, as those in the art of liquid level sensing technology will recognize.

Sensor 502 can be coupled to a microcontroller 504 (see FIG. 12) that determines the requisite action of pumps and valves necessary to achieve the desired operation. The microcontroller can further be coupled to motor 270 to increase or decrease the rotational speed of round plate 222, or to stop motion of plate 222 in the event that the liquid level has fallen below the predetermined level and cannot be increased. In a preferred embodiment of the present invention the microcontroller is implemented as a PC. Those skilled in the art will appreciate that the present invention may be practiced with other computing devices, including a laptop and other portable computers, multiprocessor systems, networked computers, mainframe computers, hand-held computers, PDAs, and on devices that include a processor, a memory, and a display. The microcontroller can also be implemented as a hard wired logical device, such as an application specific integrated circuit.

Receiver 238 can be included as part of housing 212 during fabrication, instead of being a screw in component. Receiver 238 can further be injection molded as part of housing 212. The receiver can further be removed by the user by a single-use mechanism such as a "snap off" mechanism. Such a mechanism is useful if the user wishes to store liquid 276 as a sample, or to transfer liquid 276 as a sample to another facility, such as a laboratory. User-executed separation of receiver 238 and housing 212 allows the user to handle only receiver 238 in such cases, instead of the entire receiver 238/housing 212 assembly. If receiver 238 is instead attached by a multiple-use mechanism such as a threaded drain port 236 the user has the option of removing one receiver 238 and attaching another receiver 238. This is useful if the total volume of liquid 276 exceeds the capacity of one receiver 238 or, more likely, if the user wishes to isolate different portions of liquid 276 in different containers.

The system can further include a filter 505 (see FIG. 12) disposed in or above opening 260, or opening 228, so that all incoming air passes through the filter. The filter can be any means of preventing some of the particulates in the fluid (usually air) from entering cavity 214. One example of such a filter is a size-exclusion membrane, which contains pores of a certain size such that particles larger than the pores cannot pass through the membrane. Another example of a filter is a magnetic membrane with very large pores. In this case, the membrane blocks very few particles based on size-exclusion, but removes all or nearly all magnetic particles, such as iron filings. Note iron is very massive, and unless iron is specifically a target of interest, large amounts of iron will undesirably increase the load on motor 270. Another example of a filter is an affinity-based membrane. Such a membrane would also have very large pores, excluding few particles based on size. However, the membrane would include a chemical coating, such as an antibody, that would selectively remove certain target particles from the air based on molecular binding. Yet another example of a filter is a membrane containing a chemical adsorbent. In this case, the material would adsorb, either specifically or non-specifically, chemical vapors from the incoming air. Preferably filter 505 is removable for replacement, cleaning, or recovery of the collected material.

In another embodiment to enhance performance, a slope is introduced into the top of housing 212 and in impeller vanes 224, and other associated parts. FIG. 16 illustrates a housing and impeller modified in such a fashion. On the upper outer surface 212b of housing 212a, the slope begins at the periphery of opening 260 and extends radially outward. The inner surface 212c of the upper portion of housing 212a is preferably a convex cone, with the highest part of the cone at the bottom peripheral edge of opening 260 and the lowest part of the cone at the surface where top portion of the housing meets the walls of the housing (see surface 212e). Note that cover plate 216 of FIGS. 12 and 13 has a planar configuration, not the sloped configuration of FIG. 16.

If an annular plate is to be part of the impeller (such as plate 216 in FIGS. 12 and 13), such an annular plate also preferably has a sloped surface. Annular plate 226a is generally cone shaped, having a pitch corresponding to surface 212c. Preferably, impeller vane 224e adopt the same pitch, becoming taller toward the center of round plate 222 and shorter at the outer edge of round plate 222. Impeller vane 224c clearly illustrates this configuration as well. Note that an inner portion 506 of impeller vane 224c is significantly taller than an outer portion 508 of impeller vane 224c.

The advantage of such sloped surfaces lies in the acceleration of the air that occurs as air moves from the center of round plate 222 to the outer edge of round plate 222. In an unsloped configuration, the cross-sectional area of the air flow increases in this direction, meaning that air flow would normally decelerate. By adding the slope, however, the cross sectional area can be made to increase less, stay constant, or even decrease, meaning that the air velocity can be made less decelerating, constant, or accelerating.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. An impact particle collector for separating particulates from a gaseous fluid in which the particulates are entrained, comprising:
    (a) a prime mover having a drive shaft that is drivingly rotated;
    (b) an impeller that is mechanically coupled to the drive shaft and rotated thereby, the impeller comprising a base plate and a plurality of vanes disposed on an upper surface of the base plate, such that a ratio of vane height to base plate diameter is in the range of about 0.01 to about 0.2; and
    (c) a housing for the impeller, said housing defining a fluid passage for conveying the gaseous fluid in which the particulates are entrained to the impeller, such that when the impeller is rotated by the prime mover, the gaseous fluid is drawn into the housing so that the particulates entrained in the gaseous fluid impact upon the impeller, being thereby separated from the gaseous fluid when impacted by the vanes of the impeller.

2. The impact particle collector of claim 1, wherein a base of each of the plurality of vanes extends laterally to a greater extent than does an upper surface of each vane.

3. The impact particle collector of claim 1, wherein the plurality of vanes are configured such that a height of each vane adjacent a center of the base plate is larger than a height of each vane adjacent to an outer edge of the base plate.

4. The impact particle collector of claim 1, wherein the plurality of vanes are configured such that each vane does not extend within about one millimeter of an outer edge of the base plate.

5. The impact particle collector of claim 1, wherein the plurality of vanes are substantially evenly spaced upon the upper surface of the base plate, such that when the impeller is drivingly rotated by the prime mover, the impeller presents a balanced load.

6. The impact particle collector of claim 5, wherein at least some of the plurality of vanes are truncated vanes.

7. The impact particle collector of claim 5, wherein the housing includes an opening disposed proximate a center of the base plate, and none of the vanes are disposed on a portion of the base plate directly beneath the opening.

8. The impact particle collector of claim 1, further comprising a nozzle in fluid communication with a rinse fluid reservoir, the nozzle being disposed to introduce a rinse fluid at the inward edges of the plurality of vanes, when the impeller is being rotated by the prime mover.

9. The impact particle collector of claim 1, further comprising:
  (a) a rinse fluid reservoir including a sensor configured to detect a level of rinse fluid contained within the reservoir;
  (b) a nozzle in fluid communication with the rinse fluid reservoir, the nozzle being disposed to introduce a rinse fluid into the housing to rinse particulates off of the impeller; and
  (c) a pump configured to deliver a rinse fluid from the rinse fluid reservoir to the nozzle.

10. The impact particle collector of claim 9, further comprising a microcontroller electrically coupled with the sensor, and controllably coupled to the prime mover and the pump, the microcontroller being configured to implement a plurality of functions, including at least one of:
  (a) reducing a rotational velocity of the impeller whenever a level of rinse fluid in the rinse fluid reservoir falls below a predetermined level;
  (b) reducing a volume of fluid delivered from the rinse fluid reservoir to the nozzle per unit time, whenever a level of rinse fluid in the rinse fluid reservoir falls below a predetermined level; and
  (c) de-energizing the prime mover whenever a level of rinse fluid in the rinse fluid reservoir falls below a predetermined level.

11. The impact particle collector of claim 10, further comprising a makeup reservoir in fluid communication with the rinse fluid reservoir, the makeup reservoir providing additional rinse fluid to the rinse fluid reservoir should level of rinse fluid in the rinse fluid reservoir falls below a predetermined level.

12. The impact particle collector of claim 10, wherein the rinse fluid reservoir is coupled in fluid communication with a lower portion of the housing, and said lower portion of the housing includes sloping surfaces configured to direct rinse fluid contacting the lower portion of the housing into the rinse fluid reservoir.

13. The impact particle collector of claim 1, further comprising a filter configured to filter the gaseous fluid before the gaseous fluid contacts the impeller.

14. The impact particle collector of claim 13, wherein the filter comprises a size-exclusion membrane including pores of a predetermined certain size, such that particles larger than the pores cannot pass through the membrane.

15. The impact particle collector of claim 13, wherein the filter comprises a magnetic membrane including pores of a predetermined certain size, such that nonmagnetic particles larger than the pores cannot pass through the membrane, and magnetic particles smaller than the pores cannot pass through the membrane.

16. The impact particle collector of claim 13, wherein the filter comprises an affinity-based membrane including pores of a predetermined certain size, such that particles larger than the pores cannot pass through the membrane, and particles smaller than the pores and having a corresponding affinity cannot pass through the membrane.

17. The impact particle collector of claim 16, wherein the affinity-based membrane comprises an antibody coating, such that particles having a corresponding antigen cannot pass through the membrane.

18. The impact particle collector of claim 13, wherein the filter comprises a membrane including pores of a predetermined certain size, and a incorporating a chemical adsorbent, such that particles larger than the pores cannot pass through the membrane, and chemicals absorbed by the chemical adsorbent cannot pass through the membrane.

19. The impact particle collector of claim 1, wherein the impeller has a mean surface roughness selected to increase the likelihood that a particle entrained in the gaseous fluid will adhere to the impeller.

20. The impact particle collector of claim 1, wherein the internal surfaces of the housing each have a mean surface roughness selected to decrease the likelihood that a particle entrained in the gaseous fluid will adhere to the internal surfaces of the housing.

21. The impact particle collector of claim 1, wherein the housing comprises curved internal surfaces wherever a side of the housing joins an upper portion of the housing, and wherever a side of the housing joins a lower portion of the housing, such curved internal surfaces reducing the likelihood that a rinse fluid will be undesirably retained within the housing.

22. The impact particle collector of claim 1, wherein an upper portion of the housing comprises an opening for directing a gaseous fluid toward the impeller, and an external surface of the upper portion of the housing is shaped as an inverted cone, with a base of the cone corresponding to an outer edge of the upper portion, and an apex of the cone corresponding to the opening, such that the apex of the cone is disposed lower than the base of the cone.

23. The impact particle collector of claim 1, wherein an upper portion of the housing comprises an opening for directing a gaseous fluid toward the impeller, and an internal surface of the upper portion of the housing is shaped as an inverted cone, with a base of the cone corresponding to an inner edge of the upper portion, and an apex of the cone corresponding to the opening, such that the apex of the cone is disposed higher than the base of the cone.

24. The impact particle collector of claim 1, wherein an upper portion of the housing comprises an opening for directing a gaseous fluid toward the impeller, and an external surface of the upper portion of the housing slopes away from the opening, such that a highest portion of the external surface of the upper portion of the housing corresponds to an outer edge of the upper portion, and a lowest portion of the external surface of the upper portion of the housing corresponds to a periphery of the opening.

25. The impact particle collector of claim 1, wherein an upper portion of the housing comprises an opening for directing a gaseous fluid toward the impeller, and an internal surface of the upper portion of the housing slopes away from the opening, such that a lowest portion of the internal surface of the upper portion of the housing corresponds to an inner edge of the upper portion, and a highest portion of the internal surface of the upper portion of the housing corresponds to a periphery of the opening.

26. The impact particle collector of claim 25, wherein each of the plurality of vanes includes a sloping upper surface substantially corresponding to the slope of the internal surface of the upper portion of the housing, such that a height of each vane is greater proximate a center of the base plate that a height of each vane proximate an outer edge of the base plate.

27. The impact particle collector of claim 25, wherein the impeller further comprises a top plate having an opening in a center of the top plate, the top plate having sloping upper surfaces and lower surfaces that substantially correspond to the slope of the internal surface of the upper portion of the housing, such that a lowest portion of the top plate corresponds to an outer edge of the top plate, and a highest portion of the top plate corresponds to an inner edge of the top plate proximate the opening in the top plate.

28. The impact particle collector of claim 1, wherein a gap exists between an inner surface of an upper portion of the housing and the impeller, such that the gap is designed to exceed an expected dimensional variation related to a manufacturing process used to produce the impeller.

29. The impact particle collector of claim 28, wherein the gap is about 2 millimeters.

30. The impact particle collector of claim 28, wherein the gap is about 2.2 millimeters.

* * * * *